US011630311B1

(12) United States Patent
Lewis

(10) Patent No.: US 11,630,311 B1
(45) Date of Patent: Apr. 18, 2023

(54) ENHANCED OPTICAL AND PERCEPTUAL DIGITAL EYEWEAR

(71) Applicant: Percept Technologies Inc, Los Altos, CA (US)

(72) Inventor: Scott W. Lewis, Las Vegas, NV (US)

(73) Assignee: Percept Technologies, Las Vegas, NV (US)

( * ) Notice: Subject to any disclaimer, the term of this patent is extended or adjusted under 35 U.S.C. 154(b) by 0 days.

(21) Appl. No.: 17/216,446

(22) Filed: Mar. 29, 2021

Related U.S. Application Data

(60) Continuation of application No. 16/194,236, filed on Nov. 16, 2018, now Pat. No. 10,966,239, which is a (Continued)

(51) Int. Cl.
*H04W 4/00* (2018.01)
*G02B 27/01* (2006.01)
(Continued)

(52) U.S. Cl.
CPC .......... *G02B 27/0172* (2013.01); *A61B 3/113* (2013.01); *G02B 27/0093* (2013.01);
(Continued)

(58) Field of Classification Search
CPC ................. H04W 28/04; H04W 72/04; H04W 72/042; H04W 88/08; H04W 28/0278; H04W 52/0206; H04W 72/0406; H04W 72/0413; H04W 72/12; H04W 72/1268; H04W 72/1273; H04W 72/14; H04W 84/045;
(Continued)

(56) References Cited

U.S. PATENT DOCUMENTS 4,279,474 A 7/1981 Belgorod
4,300,818 A 11/1981 Schachar
(Continued)

FOREIGN PATENT DOCUMENTS

WO WO-2021007087 A1 * 1/2021 ............ G06F 21/32

OTHER PUBLICATIONS

Vitor Fernando Pamplona, Interactive Measurement and Tailored Displays for Optical Aberrations of the Human Eye, Jul. 2012, Universidade Federal do Rio Grande do Sul, pp. 1-159. (Year: 2012).*

(Continued)

*Primary Examiner* — Phuongchau Ba Nguyen
(74) *Attorney, Agent, or Firm* — Los Altos Law

(57) ABSTRACT

Improved wearable optics is disclosed. The wearable optics comprises a frame member and a lens. The wearable optics also includes circuitry within the frame member for enhancing the use of the wearable optics. A system and method in accordance with the present invention is directed to a variety of ways to enhance the use of eye-glasses. They are: (1) media focals, that is, utilizing the wearable optics for its intended purpose and enhancing that use by using imaging techniques to improve the vision of the user; (2) telecommunications enhancements that allow the eyeglasses to be integrated with telecommunication devices such as cell phones or the like; and (3) entertainment enhancements that allow the wearable optics to be integrated with devices such as MP3 players, radios, or the like.

20 Claims, 28 Drawing Sheets

Related U.S. Application Data continuation of application No. 13/842,550, filed on Mar. 15, 2013, now Pat. No. 9,155,077, which is a continuation of application No. 13/739,929, filed on Jan. 11, 2013, now Pat. No. 9,010,929, which is a continuation of application No. 13/078,589, filed on Apr. 1, 2011, now Pat. No. 8,353,594, which is a continuation of application No. 12/621,423, filed on Nov. 18, 2009, now Pat. No. 7,918,556, which is a continuation of application No. 12/029,068, filed on Feb. 11, 2008, now Pat. No. 7,758,185, which is a division of application No. 11/245,756, filed on Oct. 7, 2005, now abandoned.

(51) Int. Cl.

| | | |
|---|---|---|
| *G02B 27/00* | (2006.01) | |
| *G02C 7/00* | (2006.01) | |
| *G02C 7/10* | (2006.01) | |
| *G06F 3/01* | (2006.01) | |
| *H04L 1/00* | (2006.01) | |
| *H04L 1/1607* | (2023.01) | |
| *H04L 5/00* | (2006.01) | |
| *H04L 5/14* | (2006.01) | |
| *H04W 28/02* | (2009.01) | |
| *H04W 52/02* | (2009.01) | |
| *H04W 72/04* | (2023.01) | |
| *H04W 72/12* | (2023.01) | |
| *H04W 72/1268* | (2023.01) | |
| *H04W 72/1273* | (2023.01) | |
| *H04W 72/14* | (2009.01) | |
| *G02C 7/12* | (2006.01) | |
| *G02C 11/00* | (2006.01) | |
| *A61B 3/113* | (2006.01) | |
| *G02B 5/30* | (2006.01) | |
| *H04W 84/04* | (2009.01) | |
| *H04W 84/12* | (2009.01) | |
| *H04W 88/08* | (2009.01) | |

(52) U.S. Cl.
CPC ............ *G02B 27/017* (2013.01); *G02C 7/00* (2013.01); *G02C 7/101* (2013.01); *G02C 7/12* (2013.01); *G02C 11/10* (2013.01); *G06F 3/011* (2013.01); *G06F 3/013* (2013.01); *H04L 1/00* (2013.01); *H04L 1/0016* (2013.01); *H04L 1/0026* (2013.01); *H04L 1/0077* (2013.01); *H04L 1/1621* (2013.01); *H04L 5/001* (2013.01); *H04L 5/0035* (2013.01); *H04L 5/0044* (2013.01); *H04L 5/0069* (2013.01); *H04L 5/0073* (2013.01); *H04L 5/14* (2013.01); *H04L 5/1469* (2013.01); *H04W 28/0278* (2013.01); *H04W 52/0206* (2013.01); *H04W 72/0406* (2013.01); *H04W 72/0413* (2013.01); *H04W 72/12* (2013.01); *H04W 72/1268* (2013.01); *H04W 72/1273* (2013.01); *H04W 72/14* (2013.01); *G02B 5/30* (2013.01); *G02B 2027/0127* (2013.01); *G02B 2027/0138* (2013.01); *G02B 2027/0141* (2013.01); *G02B 2027/0178* (2013.01); *G02B 2027/0187* (2013.01); *H04W 72/04* (2013.01); *H04W 84/045* (2013.01); *H04W 84/12* (2013.01); *H04W 88/08* (2013.01); *Y02D 30/70* (2020.08)

(58) Field of Classification Search
CPC ........ H04W 84/12; H04L 5/0007; H04L 1/00; H04L 1/0016; H04L 1/0026; H04L 1/0077; H04L 1/1621; H04L 5/001; H04L 5/0035; H04L 5/0044; H04L 5/0069; H04L 5/0073; H04L 5/14; H04L 5/1469; G02B 27/0172; G02B 27/0093; G02B 27/017; G02B 5/30; G02B 2027/0127; G02B 2027/0138; G02B 2027/0141; G02B 2027/0178; G02B 2027/0187; A61B 3/113; G02C 7/00; G02C 7/101; G02C 7/12; G02C 11/10; G06F 3/011; G06F 3/013; Y02D 30/70

See application file for complete search history.

(56) References Cited

U.S. PATENT DOCUMENTS

| | | | |
|---|---|---|---|
| 5,212,677 A | 5/1993 | Shimote et al. | |
| 5,305,012 A | 4/1994 | Faris | |
| 5,552,841 A | 9/1996 | Gallorini et al. | |
| 5,583,795 A | 12/1996 | Smyth | |
| 5,617,035 A | 4/1997 | Swapp | |
| 5,751,260 A | 5/1998 | Nappi et al. | |
| 5,886,822 A | 3/1999 | Spitzer | |
| 6,091,378 A | 7/2000 | Richardson et al. | |
| 6,099,124 A | 8/2000 | Hidaji | |
| 6,106,119 A | 8/2000 | Edwards | |
| 6,222,508 B1 | 4/2001 | Alvelda et al. | |
| 6,231,193 B1 | 5/2001 | Dillon | |
| 6,307,526 B1 * | 10/2001 | Mann | G02B 27/017 348/207.1 |
| 6,603,443 B1 | 8/2003 | Hildebrand et al. | |
| 6,608,615 B1 | 8/2003 | Martins | |
| 6,647,269 B2 | 11/2003 | Hendry et al. | |
| 6,836,669 B2 | 12/2004 | Miyake et al. | |
| 6,963,454 B1 * | 11/2005 | Martins | G02B 13/16 359/636 |
| 7,370,016 B1 | 5/2008 | Hunter et al. | |
| 7,436,568 B1 | 10/2008 | Kuykendall, Jr. | |
| 7,486,926 B2 | 2/2009 | White et al. | |
| 7,538,744 B1 | 5/2009 | Liu et al. | |
| 7,539,175 B2 | 5/2009 | White et al. | |
| 7,561,143 B1 | 7/2009 | Milekic | |
| 7,651,220 B1 | 1/2010 | Pattikonda | |
| 7,677,734 B2 | 3/2010 | Wallace | |
| 7,693,384 B2 | 4/2010 | Lee et al. | |
| 7,738,179 B2 | 6/2010 | Nishi | |
| 7,758,185 B2 | 7/2010 | Lewis | |
| 7,918,556 B2 | 4/2011 | Lewis | |
| 8,238,926 B2 | 8/2012 | Lewis | |
| 8,275,382 B2 | 9/2012 | Lewis | |
| 8,282,212 B2 * | 10/2012 | Hillis | G02C 7/085 351/205 |
| 8,353,594 B2 | 1/2013 | Lewis | |
| 8,451,850 B2 | 5/2013 | Lewis | |
| 8,566,894 B2 | 10/2013 | Lewis | |
| 8,594,636 B2 | 11/2013 | Lewis | |
| 8,696,113 B2 * | 4/2014 | Lewis | A61B 3/113 351/158 |
| 8,733,927 B1 * | 5/2014 | Lewis | G06F 3/013 351/158 |
| 8,733,928 B1 * | 5/2014 | Lewis | A61B 3/113 351/158 |
| 8,830,963 B2 | 9/2014 | Lewis | |
| 8,885,882 B1 | 11/2014 | Yin et al. | |
| 9,010,929 B2 | 4/2015 | Lewis | |
| 9,061,025 B2 | 6/2015 | Burstein et al. | |
| 9,230,292 B2 | 1/2016 | Amin et al. | |
| 9,235,064 B2 | 1/2016 | Lewis | |
| 9,239,473 B2 | 1/2016 | Lewis | |
| 9,244,293 B2 | 1/2016 | Lewis | |
| 9,264,319 B2 | 2/2016 | Lewis | |
| 9,323,325 B2 | 4/2016 | Perez et al. | |
| 9,363,541 B2 | 6/2016 | Lewis | |
| D784,362 S | 4/2017 | Amin | |
| 9,658,473 B2 * | 5/2017 | Lewis | A63F 13/5255 |
| 9,740,552 B2 | 8/2017 | Lewis | |
| 9,843,897 B1 | 12/2017 | Lin et al. | |
| 10,021,430 B1 | 7/2018 | Lewis | |
| 10,091,084 B2 | 10/2018 | Tao et al. | |

(56) References Cited

U.S. PATENT DOCUMENTS

| | | | |
|---|---|---|---|
| 10,093,252 B2 | 10/2018 | Zych | |
| 10,151,937 B2 | 12/2018 | Lewis | |
| 10,185,147 B2 * | 1/2019 | Lewis | H04W 72/12 |
| 10,521,661 B2 * | 12/2019 | Chen | G06V 40/19 |
| 10,795,183 B1 * | 10/2020 | Lewis | G02C 7/104 |
| 10,962,789 B1 * | 3/2021 | Lewis | A61B 3/113 |
| 10,966,239 B1 * | 3/2021 | Lewis | G02C 7/101 |
| 11,181,740 B1 * | 11/2021 | Lewis | A61B 3/113 |
| 11,209,654 B1 * | 12/2021 | Lewis | A61B 3/113 |
| 11,294,203 B2 * | 4/2022 | Lewis | G02C 7/104 |
| 11,428,937 B2 * | 8/2022 | Lewis | H04W 72/14 |
| 2001/0029583 A1 | 10/2001 | Palatov et al. | |
| 2001/0055152 A1 | 12/2001 | Richards | |
| 2002/0044152 A1 | 4/2002 | Abbott, III et al. | |
| 2002/0046122 A1 | 4/2002 | Barber et al. | |
| 2002/0056118 A1 | 5/2002 | Hunter et al. | |
| 2002/0075210 A1 | 6/2002 | Nestorovic et al. | |
| 2002/0102993 A1 | 8/2002 | Hendrey et al. | |
| 2002/0105482 A1 | 8/2002 | Lemelson et al. | |
| 2002/0140899 A1 | 10/2002 | Blum et al. | |
| 2002/0181115 A1 * | 12/2002 | Massof | G02B 27/017 |
| | | | 359/630 |
| 2002/0188219 A1 | 12/2002 | Suchard | |
| 2003/0001981 A1 | 1/2003 | Milne | |
| 2003/0071962 A1 | 4/2003 | Nishihara | |
| 2003/0142041 A1 | 7/2003 | Barlow et al. | |
| 2003/0161354 A1 | 8/2003 | Bader et al. | |
| 2004/0100567 A1 * | 5/2004 | Miller | H04N 1/2112 |
| | | | 348/E5.047 |
| 2004/0101178 A1 * | 5/2004 | Fedorovskaya | H04N 1/32 |
| | | | 382/128 |
| 2004/0103111 A1 * | 5/2004 | Miller | G06V 40/193 |
| | | | 707/999.102 |
| 2004/0108971 A1 | 7/2004 | Waldern et al. | |
| 2004/0148551 A1 | 7/2004 | Kawahara | |
| 2004/0156554 A1 | 8/2004 | McIntyre | |
| 2005/0020910 A1 | 1/2005 | Quadling et al. | |
| 2005/0049022 A1 | 3/2005 | Mullen | |
| 2005/0057701 A1 | 3/2005 | Weiss | |
| 2005/0175218 A1 | 8/2005 | Vertegaal et al. | |
| 2005/0206583 A1 | 9/2005 | Lemelson et al. | |
| 2005/0211764 A1 | 9/2005 | Barcelou | |
| 2005/0246282 A1 | 11/2005 | Naslund et al. | |
| 2005/0249196 A1 | 11/2005 | Ansari et al. | |
| 2006/0023158 A1 | 2/2006 | Howell et al. | |
| 2006/0023595 A1 | 2/2006 | Erickson et al. | |
| 2006/0050232 A1 | 3/2006 | Dukes et al. | |
| 2006/0075441 A1 | 4/2006 | Gauba et al. | |
| 2006/0093998 A1 * | 5/2006 | Vertegaal | H04N 7/18 |
| | | | 705/7.29 |
| 2006/0132382 A1 | 6/2006 | Jannard | |
| 2006/0140502 A1 | 6/2006 | Tseng et al. | |
| 2006/0158639 A1 | 6/2006 | Campin et al. | |
| 2006/0146275 A1 | 7/2006 | Mertz | |
| 2006/0244908 A1 | 11/2006 | Cano | |
| 2006/0282864 A1 | 12/2006 | Gupte | |
| 2007/0002039 A1 | 1/2007 | Pendleton et al. | |
| 2007/0143793 A1 | 6/2007 | Barratt et al. | |
| 2007/0153498 A1 | 7/2007 | Wilt et al. | |
| 2007/0161972 A1 | 7/2007 | Felberg et al. | |
| 2007/0226575 A1 | 9/2007 | Zhang et al. | |
| 2007/0282678 A1 | 12/2007 | Dendi et al. | |
| 2008/0062378 A1 | 3/2008 | McCracken | |
| 2008/0186449 A1 | 8/2008 | Sur et al. | |
| 2008/0316605 A1 | 12/2008 | Hazell et al. | |
| 2009/0103044 A1 | 4/2009 | Duston et al. | |
| 2009/0207373 A1 | 8/2009 | Stinson | |
| 2009/0209723 A1 | 8/2009 | Lesartre et al. | |
| 2009/0216092 A1 | 8/2009 | Waldorf et al. | |
| 2009/0268162 A1 | 10/2009 | Stetson et al. | |
| 2010/0002191 A1 | 1/2010 | Drobe | |
| 2010/0045928 A1 | 2/2010 | Levy | |
| 2010/0067335 A1 | 3/2010 | Li et al. | |
| 2010/0149073 A1 | 6/2010 | Chaum et al. | |
| 2010/0305411 A1 | 12/2010 | Paul | |
| 2011/0007275 A1 | 1/2011 | Yoo et al. | |
| 2011/0213664 A1 | 9/2011 | Osterhout et al. | |
| 2012/0019662 A1 | 1/2012 | Maltz | |
| 2012/0021806 A1 | 1/2012 | Maltz | |
| 2012/0088526 A1 | 4/2012 | Linder | |
| 2012/0154277 A1 | 6/2012 | Bar-Zeev et al. | |
| 2012/0229248 A1 | 9/2012 | Pashionikar et al. | |
| 2012/0235902 A1 | 9/2012 | Eisenhardt et al. | |
| 2012/0242678 A1 | 9/2012 | Border et al. | |
| 2012/0293548 A1 | 11/2012 | Perez et al. | |
| 2012/0293773 A1 | 11/2012 | Publicover et al. | |
| 2012/0294478 A1 * | 11/2012 | Publicover | G02B 27/017 |
| | | | 348/78 |
| 2012/0329764 A1 | 12/2012 | Burstein et al. | |
| 2013/0117377 A1 | 5/2013 | Miller | |
| 2013/0156265 A1 | 6/2013 | Hennessy | |
| 2013/0293844 A1 | 11/2013 | Gross et al. | |
| 2014/0002796 A1 | 1/2014 | Marcos Munoz | |
| 2014/0303124 A1 | 10/2014 | Burstein et al. | |
| 2014/0347265 A1 | 11/2014 | Aimone et al. | |
| 2015/0241706 A1 * | 8/2015 | Schowengerdt | G06V 10/42 |
| | | | 345/633 |
| 2018/0177976 A1 | 6/2018 | Burstein | |

OTHER PUBLICATIONS

DOHI, Lecture Notes in Computer Science.

* cited by examiner

100

102'

300

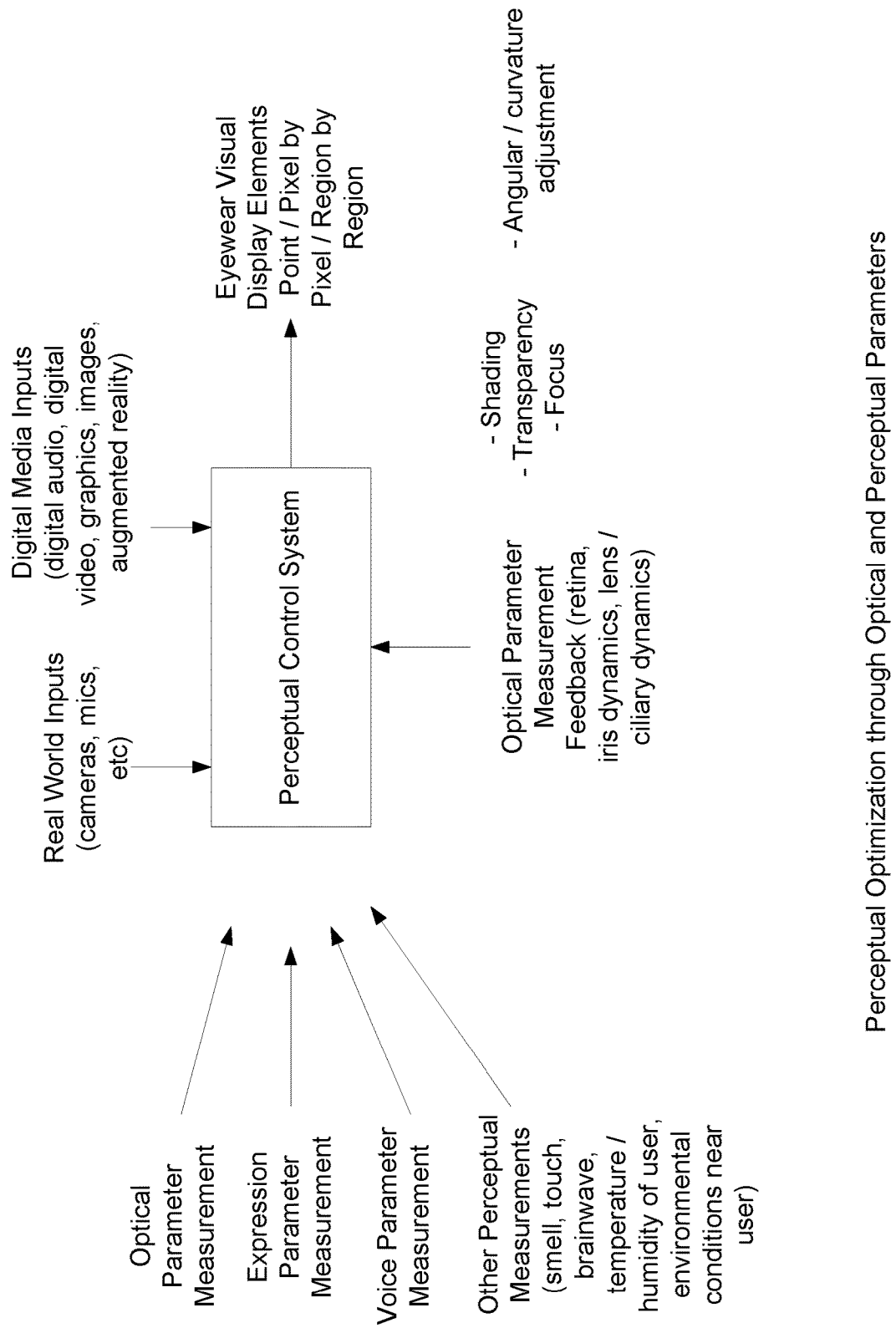

Optical Parameters

700
Social Networking

800
Messaging

1200

1600
Gaming (Online/mobile)

Optical/Perceptual – Operating System

2100
System Simulator

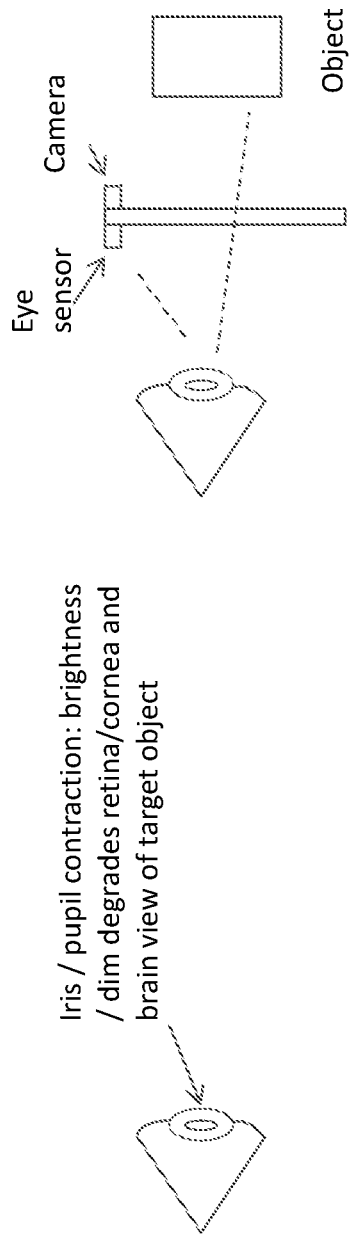

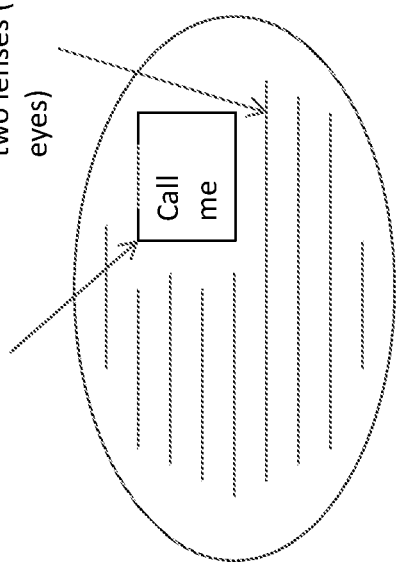

Shading or translucent background follows object in real time
-shading optimized by tracking object and shading independently in each of two lenses (left and right eyes)

Object normal brightness

Call me

Viewing Plane
After
Figure 22F

Inverse Shading

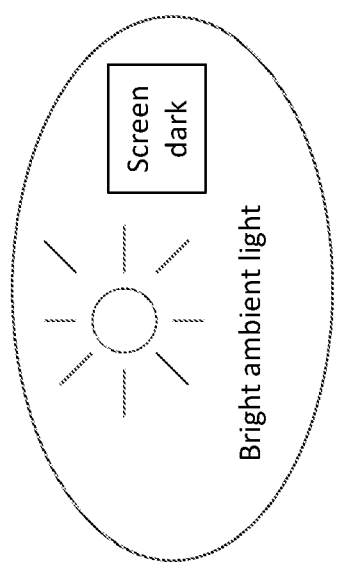

Phone screen appears dark since ambient light is brighter than screen

Screen dark

Bright ambient light

Viewing Plane
Before
Figure 22E

Eye tracking illumination and enhanced efficiency

ENHANCED OPTICAL AND PERCEPTUAL DIGITAL EYEWEAR

CROSS-REFERENCE TO RELATED APPLICATIONS

Under 35 U.S.C. 120, this application is a continuation application and claims priority to U.S. application Ser. No. 14/921,926, filed on Oct. 23, 2015, entitled "ENHANCED OPTICAL AND PERCEPTUAL DIGITAL EYEWEAR,"

which is a continuation application and claims priority to U.S. application Ser. No. 13/841,550, filed on Mar. 15, 2013, entitled "ENHANCED OPTICAL AND PERCEPTUAL DIGITAL EYEWEAR,"

which is a continuation-in-part and claims the benefit of priority to U.S. patent application Ser. No. 13/739,929, filed on Jan. 11, 2013, entitled "DIGITAL EYEWEAR", which is a continuation application of U.S. patent application Ser. No. 13/078,589, filed on Apr. 1, 2011, entitled "DIGITAL EYEWEAR", now U.S. Pat. No. 8,353,594, issued on Jan. 15, 2013, which is a continuation application of U.S. patent application Ser. No. 12/621,423, filed on Nov. 18, 2009, entitled "DIGITAL EYEWEAR", now U.S. Pat. No. 7,918,556, issued on Apr. 5, 2011, which is a continuation application of U.S. patent application Ser. No. 12/029,068, filed Feb. 11, 2008, entitled "DIGITAL EYEWEAR", now U.S. Pat. No. 7,758,185, issued on Jul. 20, 2010, which is a divisional application of U.S. patent application Ser. No. 11/245,756, filed Oct. 7, 2005, entitled "DIGITAL EYEWEAR", all of which are incorporated herein by reference.

This application is related to U.S. Pat. No. 8,696,113 (Docket No. 5266P), issued on Apr. 15, 2014, entitled "Enhanced Optical and Perceptual Digital Eyewear", which is also incorporated herein by reference.

FIELD OF THE INVENTION

The present invention relates generally to wearable optics and more particularly to wearable optics that includes additional functionality.

BACKGROUND OF THE INVENTION

Wearable optics is utilized for a variety of purposes. Wearable optics is used for improving one's vision for reading glasses and to protect one's vision. Oftentimes protective goggles are used to protect eyes within dangerous areas. It is desirable to add additional functionality to glasses. This functionality can include a variety of forms, which are electronic, mechanical, aesthetic, etc. Accordingly, it is always desired to provide additional functionality to wearable optics. What is desired is a system and method which will increase the functionality of glasses beyond their normal use while still maintaining them for their primary uses. The present invention addresses such a need.

SUMMARY OF THE INVENTION

A wearable optics device and method of use is disclosed. In a first aspect a method comprises utilizing dynamic eye tracking with a wearable optics device; wherein parameters personalized to a user can be provided based upon the dynamic eye tracking.

In a second aspect, a wearable optics device comprises a lens and a dynamic eye tracking mechanism in communication with the lens. Parameters personalized to a user can be provided based upon the dynamic eye tracking.

In a third aspect, a method comprises utilizing dynamic eye tracking with a wearable optics device. A perceptual optimization is utilized based upon the dynamic eye tracking.

In a fourth aspect, a wearable optics device comprises a lens and a dynamic eye tracking mechanism in communication with the lens. A perceptual optimization is utilized based upon the dynamic eye tracking.

In a fifth aspect, a method comprises utilizing dynamic eye tracking with a wearable optics device. An augmented reality overlay is utilized based upon the dynamic eye tracking.

In a sixth aspect, a wearable optics device comprises a lens; and a dynamic eye tracking mechanism in communication with the lens. An augmented reality overlay is utilized based upon the dynamic eye tracking.

In a seventh aspect, a method comprises utilizing dynamic eye tracking with a wearable optics device. Augmented reality navigation is utilized based upon the dynamic eye tracking.

In an eighth aspect, a wearable optics device comprises a lens; and a dynamic eye tracking mechanism in communication with the lens. Augmented reality navigation is utilized based upon the dynamic eye tracking.

BRIEF DESCRIPTION OF THE DRAWINGS

FIG. 5B illustrates perceptual optimization utilizing optical and perceptual parameters.

FIG. 22A thru FIG. 22F illustrate the embodiment of inverse shading using the wearable optics device.

DETAILED DESCRIPTION

The present invention relates generally to wearable optics and more particularly to wearable optics that includes additional functionality. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

A system and method in accordance with the present invention is directed to a variety of ways to enhance the use of wearable optics devices.

To describe the features of the present invention in more detail refer now to the following description in conjunction with the accompanying figures.

1. Media Focals 100

FIG. 1

Figure 1:
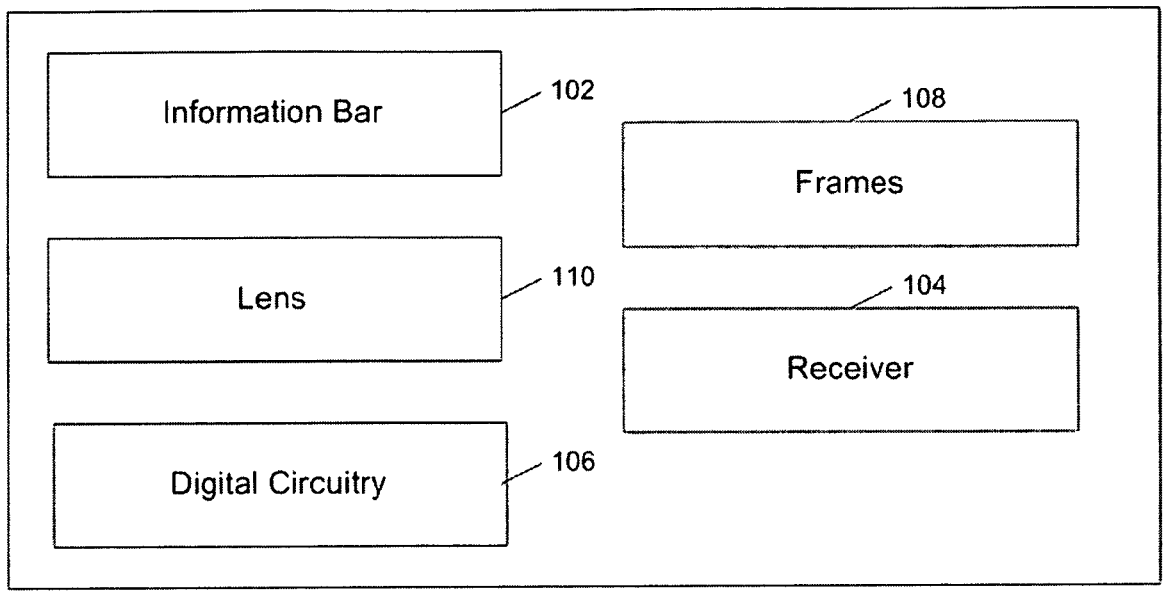
FIG. 1 is a diagram that illustrates media focals.

FIG. 1 is a diagram that illustrates Media focals 100. Media focals 100 comprises an information bar 102, receiver 104, digital circuitry 106, frames 108 and lens 110. Media focals 100 allow for enhancing the wearable optics for its primary purpose, for example, a digital camera could be placed within the wearable optics to allow for seeing certain of these images. For example, the circuitry 106 for the media focals 100 could be placed within the frame 108 of the wearable optics. The lens 110 could have a totally reflective surface, or a partially reflective surface using LCDs or the like. In effect the wearable optics could look like see-through glasses, but through the use of the circuitry 106 within the wearable optics it is actually a media focal. Additionally, the wearable optics could incorporate a camera to project the user onto a second lens to achieve a see-through effect.

In a preferred embodiment, an information bar 102 is provided across a portion of the wearable optics which is visible to the user. This information bar 102 is used to convey a variety of types of information.

FIG. 2

Figure 2:
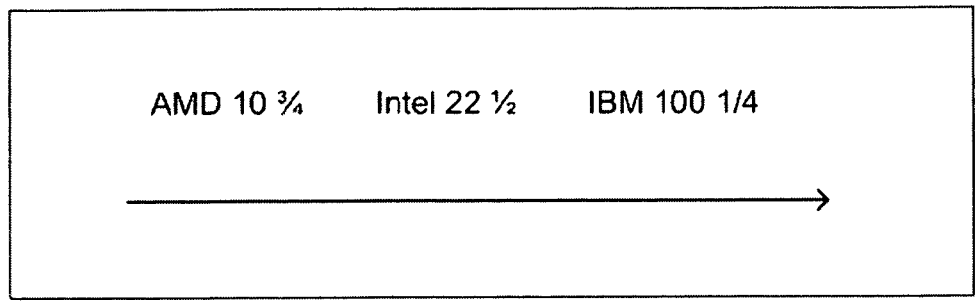
FIG. 2 comprises an information bar on media focal wearable optics.

FIG. 2 comprises an information bar 102' on media focal wearable optics. The information bar 102' can be a stock ticker scrolling across the top portion of the wearable optics, as is shown in FIG. 2. Although the information bar 102' is shown displaying a stock ticker, other kinds of information such as song titles, lyrics and the like could be displayed in the information bar. This information bar is referred to as E-focals. This information might be provided from a digital receiver through an FM station, through a cellular wireless device, or an MP3 player. Additional functionality of the E-focal will be described with more detail with respect to the cell phone enhancements as well as the music player enhancements.

One of the key features of the media focals 100 is the use of the media focals to enhance the primary function of the user, that is, being able to more accurately and clearly see the objects. In such an environment, for example, it is possible to have a zoom feature circuit to allow for the use of the wearable optics as binoculars. This would allow for the user to see objects more closely based on certain activities of the user. For example, there may be eye or pressure sensors on the wearable optics that will activate the binocular circuitry in the glasses which could receive visual data through a camera, CCD receiver of the like.

In the preferred embodiment, the circuitry 106 would be located somewhere in the frame of the glasses to provide this functionality and as circuits became smaller and devices became smaller it would be easier and easier to embed the circuitry that is well known for use for such functions directly within the device. The circuitry 106 in the device could be, for example, eye sensors which could be pressure sensors, capacitive sensors or some other type of sensor for allowing the eyes to direct the activities. Eye movement sensors, for example, could be used to activate and control the binocular glasses. Similarly, a digital camera could be put on the glasses that would allow the same kinds of technology to take pictures by the person directly.

In a similar vein, the glasses could be used as a normal corrective lens glass utilizing the digital imagery, so that, for example, a user has a certain prescription that they use with their normal prescription glasses to view an object clearly. As the user's eyes change, it would be possible that an optometrist could download the new prescription to the wearable optics such that a digital transformation of the image information is provided which is compatible with the new prescription.

Also, in a preferred embodiment a method for sensing and controlling the digital media could be implemented in a variety of ways. For example, an activity of the eye itself would control the activity of the media focal. So, for example, if the idea was to zoom the image, the eye would blink twice. It would also be possible to detect facial and eye movements (squinting, for example), as well as changes in the pupil and iris.

In a further embodiment, it would be possible for the eyeglasses in accordance with the present invention to function within a client/server model or Bluetooth (Wi-Fi) model. Utilization of the client/server model and Bluetooth Wi-Fi would make possible, for example, the display of live news or special reports (such as financial reports) from the Internet or similar sources on the eyeglasses. This would also allow for portions of circuitry to be located remotely such that less circuitry in the wearable optics is required.

The wearable optics could also include a logo, for example, law enforcement officers could have their glasses emblazoned with "Police", "Sheriff", "MP", etc.; young people could have their eyeglasses emblazoned with words and images that reflected their favorite performers, etc.; sports teams could offer the eyeglasses at discount with team monograms, etc. They could also be purchased by companies, emblazoned with the company logos, and given out as retirement gifts, etc.

2. Music Environment

FIG. 3

Figure 3:
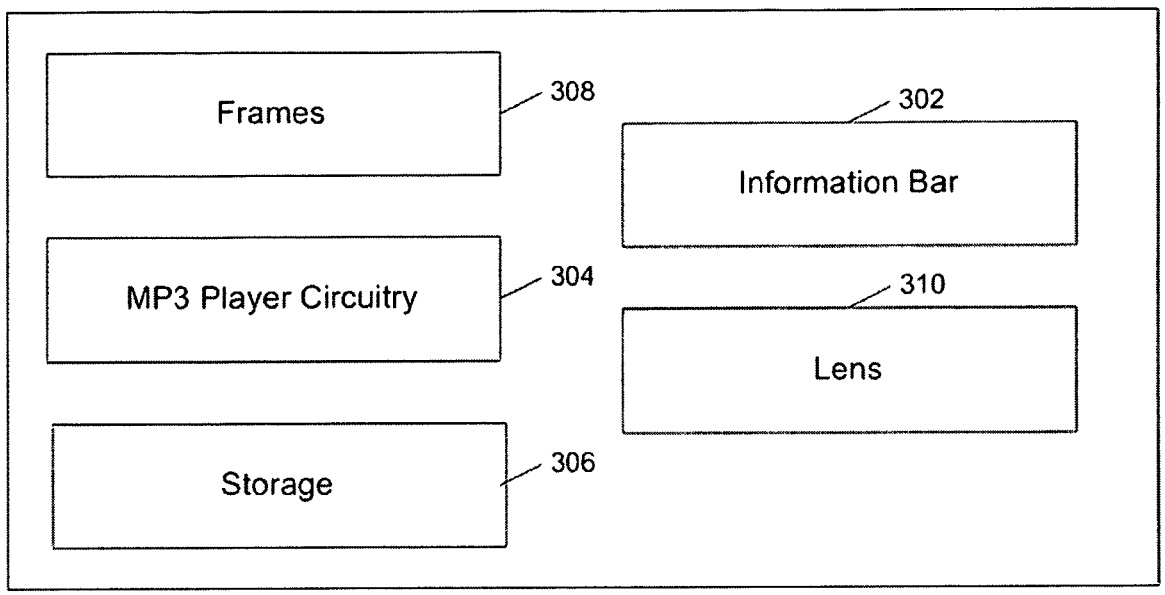
FIG. 3 is a block diagram of wearable optics that is utilized in a music environment such as an MP3 player.

FIG. 3 is a block diagram of wearable optics 300 that is utilized in a music environment such as an MP3 player. FIG. 3 comprises wearable optics 300, an information bar 302, MP3 player circuitry 304, storage 306, frames 308, and one or a plurality of lenses 310. Another environment as has been above described is the music environment. What would be desirable would be to provide music glasses in which an MP3 player on an IPod or the like is incorporated in the wearable optics, either in a wired or wireless environment. Through the use of this type of system, a plurality of users could be networked via an MP3 player type environment within a hotspot, or the like, which would allow one to have downloads of whatever music is required through the eyeglasses. The system could allow for downloadable music which could be selected via scrolling and the like through voice recognition systems.

By connecting to a client-server network or Bluetooth Wi-Fi installation, for example, the eyeglasses could link to a multimedia network, authorize downloading and billing for selected music. By this means, access to a plurality of libraries for music selections could be provided.

It would also be possible to provide access to streaming audio media. Also, access can be provided to multimedia libraries, etc., via the client/server model.

Information could be received via a digital client/server model enabled to work with iPods or MP3 players. Similarly, bluetooth wireless technology could be utilized to provide access to music and live audio sources.

The wearable optics could also be utilized in conjunction with wireless technology to allow a user or a plurality of users to participate simultaneously in single or group karaoke singing. The wearable optics could be used specifically to display the lyrics of a song, melody, notes, name of the song or other associated references.

It would also be possible to receive and listen to AM or FM radio signals, via an AM/FM radio tuner connected to the wearable optics hardware.

In this type of environment, the headphones can be either digital or analog. The user doesn't need to have 10,000 songs, for example. They can come enrolled in an in-song virtual network library upon entering a hotspot. Therefore, the local storage 306 could be limited. In addition, this would provide location identity information for one who is using the network. The songs can be streamed as well as downloaded. The songs could be purchase using the wearable optics. The system could be scalable; depending upon what kind of device was being used.

3. Telecommunications Environment

FIG. 4

Figure 4:
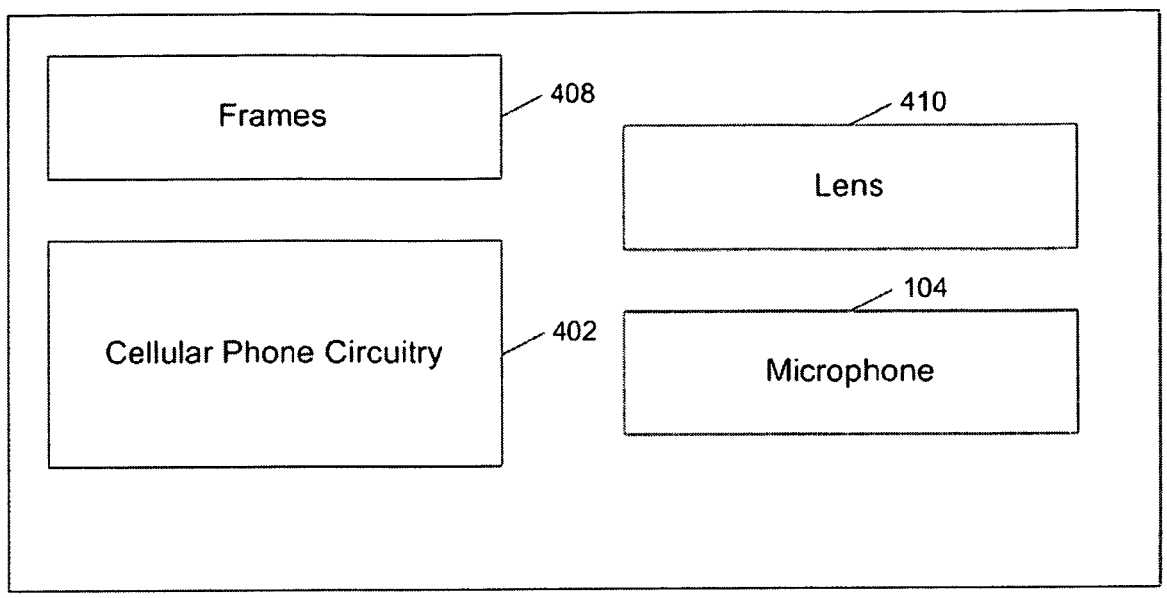
FIG. 4 is a block diagram that illustrates wearable optics that is utilized as a cell phone.
Figure 5A:
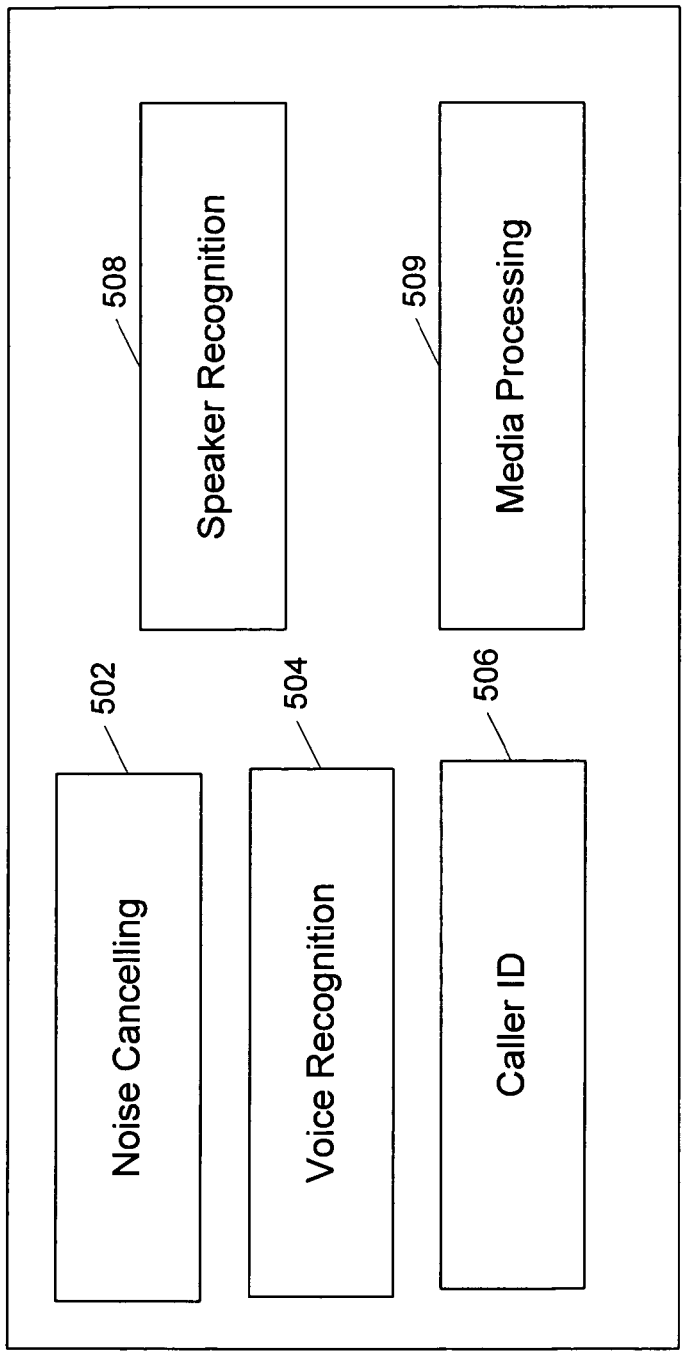
FIG. 5A is a block diagram that illustrates the cellular phone circuitry of FIG. 4.

FIG. 4 is a block diagram that illustrates wearable optics that is utilized as a cell phone 400. FIG. 4 comprises cellular phone circuitry 402, a microphone 104, frames 408 and one or a plurality of lenses 410. The cell phone wearable optics 400 could be implemented utilizing digital telephone technology. Circuitry 402 within the wearable optics could be utilized to allow a telephone number or other visual information such as that provided by multimedia messaging services to be displayed on the lens 410 of the wearable optics as shown in FIG. 3. FIG. 5 is a block diagram that illustrates the cellular phone circuitry of FIG. 4. FIG. 5 comprises noise cancelling circuitry 502, voice recognition circuitry 504, caller ID circuitry 506 and speaker recognition circuitry 508 and media processing circuits 509. The telephone number could be activated via the digital circuitry 402 as part of the media focals 100. In addition, the circuitry could be made truly digital via a digital signal processor which is coupled to a camera otherwise in the environment. The above system would allow for voice recording through use of a microphone 104 and would allow for voice recognition through use of the voice recognition circuitry 504, which would allow for signal conditioning on the cell phone in a variety of ways.

The cell phone environment 402 provides a plurality of areas for improvement utilizing existing technologies. Firstly, one of the major annoyances in cell phone use is that the users have to speak in a loud manner because of background noise and the like. There are a variety of reasons for this problem including the placement of the microphone of the cell phone relative to the speaker's mouth, due to the aforementioned background noise, and other issues. By placing the microphone 104 strategically on the wearable optics such as near the noise or mouth the user will not have to speak as loudly. The microphone could also be located in flip down microphones. In addition noise canceling circuitry 502 could be utilized to remove the background noise. The microphone capability would include the advantage of utilizing noise rejection techniques. Buttons located on the wearable optics can be utilized to control features thereon. Finally, the microphone 104 could utilize whisper technology such that the speaker will not have to speak as loudly.

FIG. 5 (continued)

The wearable optics would in a preferred embodiment include voice recognition circuitry 504 and caller ID circuitry 506. The conventionality for hearing and talking in a preferred embodiment would be located in ear and nose pad portions of glasses. Referring back to FIG. 3, the electronics for the cell phone in a preferred embodiment would be within the frame 308 of the wearable optics. In addition the wearable optics would include a fully integrated information bar 302. Finally, a speaker recognition algorithm 508 as shown in FIG. 5 would allow only the voice of the user to be recognized and the background noise would be cancelled. Accordingly, the unique characteristics of the speaker are provided via an audible model.

This can performed utilizing a variety of methods. For example analyzing the voice of the user and combining the analysis with noise cancellation. In another example the user can talk softly and cancel noise and a directional microphone is used which takes advantage of device location.

Similar to the media focal and MP3 player environments, a digital client/server or Bluetooth/wifi model could be adapted to link the wearable optics to external communication equipment. Such equipment could include digital cell phones, PDAs or wifi enabled PCs or other devices. Such an embodiment could enable review of voicemail, screen viewed emails, text to speech audio email conversions, multimedia messaging services, and other data sources.

Wireless or Bluetooth interconnection could also make possible VOIP glasses to be utilized instead of a cell phone.

Other features enabled by a wireless link could link the eyewear to MP3 devices, an iPod, a printer, wireless/wired TV, coupons, and the like. Also "PDA glasses" could provide built in a time display, alarm calendar, interfacing with PCs or network sources, a speaker and the like.

As can be seen from the above description, digital eyewear is a rapidly evolving field with from the early innovation of digital eyewear with eye tracking capabilities thru Lewis ('185 filed February 2008), to eyewear with more complex lenses and communication/display capabilities (Lewis '556, filed November 2009), to more enhancements and capabilities (Lewis '594, filed April 2011). As technology progresses to make sensors, cameras, processors, and circuitry smaller, more and more capabilities become possible to implement using digital eyewear. This enhanced digital eyewear can be used to solve important areas ranging from superior vision enhancement and mobile advertising, to use in dental/medical procedures and physical and Internet navigation. The application and value of the enhanced eyewear is increased even further when combined with augmented reality, social networking, messaging, and communications.

With the introduction and use of new materials for lens and filter integration new enhancements and capabilities of the digital eyewear can be further realized. These materials include advances in OLED, LED, transparent LED, flexible LED, crystalline, prism, holographic, polarizing, and translucent material and the like to electrorefractive, electrodiffractive, electroreflective, composite refractive materials and the like, with one or more lens material layers and passive or active display or projection based implementations.

With these new capabilities an important new set of optical and perceptual parameters can be measured and used as inputs, controls, or feedback elements that increase even further uses and value of the eyewear and lead to important improvements that can be used for teaching, sports, health, and improved perception.

Accordingly systems and methods in accordance with embodiments are disclosed that provide these enhanced features for wearable optics devices. To describe these features and embodiments in more detail refer now to the following description in conjunction with the following discussion. A key feature associated with these enhancements is providing a variety of perceptual parameters that can be utilized with the wearable optics devices. Examples of perceptual parameters include but are not limited to optical expression, voice, brain wave, environmental, audio, video, navigational, augmented reality, algorithmic, spatial, cognitive, interpretive.

FIG. 5B

FIG. 5B illustrates a perceptual optimization system 550. The perceptual optimization system 550 receives a variety of inputs including optical parameter measurements, real world inputs, digital media inputs, expression parameter measurements, optical parameter measurement feedback, other parameter measurements to provide wearable optics visual display elements. Optical parameter measurements include for example, ciliary, pupil, corneal, lens, iris, eye lid, retina measurements. Real world inputs could be for example inputs from one or more microphones or cameras. Digital media inputs could be for example from digital audio, digital video, graphics, images and augmented reality.

Other perceptual parameters could be for example, smell, touch, brainwave, temperature/humidity of the user, environmental conditions near the user. The optical feedback could be provided through information received about the retina/iris dynamics and/or the lens ciliary dynamics.

FIG. 5C

Figure 5C:
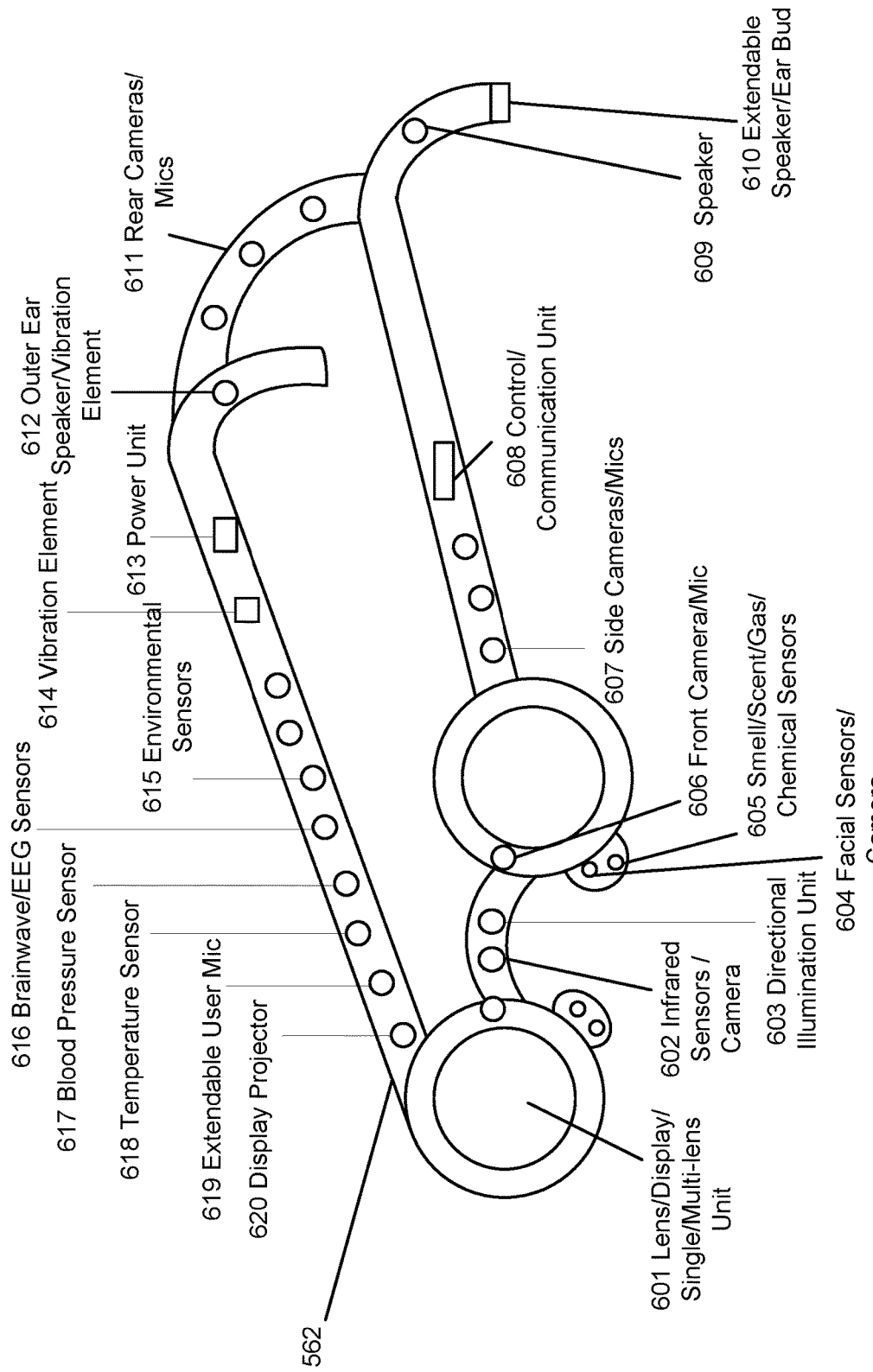
FIG. 5C illustrates the enhanced digital eyewear architecture.

FIG. 5C illustrates a wearable optics device architecture 560 in accordance with an embodiment. The architecture includes a frame 562 which includes a plurality of sensors on various areas thereon. Biometric sensors include a blood pressure sensor 617, temperature sensor 618, EEG sensor 616 and the like. Environmental sensors 615 are also provided. There are microphone sensors 606, 607, 611 on various areas of the frame. Included on the frame 562 are cameras rear, front and side 606, 607, 611 to detect objects. Within the lens is a lens display 601. A display projector 620 is provided thereon to project images on the lens display 601. The lens display 601 can be a single unit or multiple unit lens. There are infrared sensors 602 as well as a directional illumination unit 603 on the bridge of the architecture 560. There are facial and mouth movement sensors 604 and or cameras located on the lens holder of the architecture 560. There is a speaker and n extendable speaker 610 located on the frame when worn. The speaker 610 could be held in place with a head band. An outer ear speaker/vibration element 612 is provided thereon. A control communication unit 608 is utilized to control the architecture 560. A power unit can be utilized to enable the architecture. Typically the power unit 613 comprises a rechargeable battery. The battery can be charged via a connector, such as but not limited to an USB connector to a charging device laptop, tablet or desktop PC for example. In addition the device could be solar powered either by solar cells being placed on the device or the solar cells could be placed on articles of clothing (i.e. hat, shirt or pants for example) to facilitate the charging thereof. The architecture 560 includes a directional illumination unit 603, smell sensors 605 and an extendable user microphone 619.

In an embodiment, the sensors may comprise any or any combination of gyroscopes, accelerometers, torque sensors, weight sensors, pressure sensors, magnetometers, temperature sensors, light sensor, cameras and microphones, GPS, wireless detection, altitude sensors, blood pressure, heart rate sensors, biometric sensors, radio frequency identification (RFID), near field communication (NFC), mobile communication, Wi-Fi, strain gauges, fingerprint sensors, smell sensors gas sensors, chemical sensors, color sensors, sound sensors, acoustic sensors, ultraviolet sensors, electric field sensors, magnetic field sensors, gravity sensors, wind speed sensors, wind direction sensors, compass sensors, geo-locator sensor, polarized light sensors, infrared emitter sensors.

This architecture can be utilized with a conventional mobile operating system such as Android or IOS or with a new operating system incorporating optical parameters and perceptual parameters for even further capabilities and enhanced perception—eye optical or perceptual operating system (eyePOS). By using this approach and capability set, a whole new class of custom applications ("apps") can be created using the standard mobile operating systems or eyePOS and an eyePOS simulator to address manifold valuable applications that can improve human learning, entertainment, and health on one side to new navigation systems (physically linked and search linked) and enhanced perception. To describe these feature in more detail refer now to the following description.

A method and system in accordance with an embodiment comprises utilizing dynamic eye tracking with a wearable optics device; wherein parameters personalized to a user can be provided based upon the dynamic eye tracking. The method and system which includes providing an enhancement utilizing objective and subjective quality standards based upon perceptual parameters. The perceptual parameters include any and any combination of optical expression, voice, brain wave, environmental, audio, video, navigational, augmented reality, algorithmic, spatial, cognitive, interpretive. The wearable optics device controls any or any combination of mimics, amplifies, or expands a user perceptual physiology utilizing perceptual parameters.

The wearable optics device can include one or more inserts into eyeglasses. The eyeglasses comprise quad state eyeglasses. Shading control can be utilized on the wearable optics device. The shading control can be provided by one or more projectors within the wearable optics device. An occlusion effect can be projected on a lens of the wearable optics device. The shading can be provided on a lens of the wearable optics device wherein the surrounding area is occluded or reversed. The shading is provided by a polarized filter. The shading control can be provided by the lenses within the wearable optics device. The shading can be controlled using optical parameters. The optical parameters include any or any combination of ciliary, pupil, corneal, lens, iris, eye lid, and retina measurements. Materials that can electrically control any or any combination of chromatic, refractive, diffractive, transparent, reflective properties of the wearable optics device are utilized with the dynamic eye tracking. The lens can be any or any combination of transparent LCD, LED, OLED, flexible LED, flexible OLED, transparent matrix, semi-transparent matrix, prism based, holographic, electroluminescence, eletroreflective, dynamic filtering materials.

The wearable optics device comprises an electrochromatic material. In a system and method in accordance with an embodiment one or more elements are utilized within the wearable optics device to provide image information into the eye. The one or more elements include any or any combination of a lens projector, retinal projection. The retinal projection or projector plus prism provide the occlusion.

The wearable optics device includes shading control for the eyewear. In the wearable optics device, portions of an image viewed by the wearable optics device can be shaded to control brightness. The lenses of the wearable optics device can be controlled polarizing, transparent OLED, or projection and prism lenses.

The parameters my include any or any combination of prescriptions for improving the vision of a user, a zoom feature, a microscope feature, magnifying feature, retinal projection feature. The wearable optics device can be utilized in a simulator. In an embodiment, a focal of the wearable optics device is utilized in conjunction with the dynamic eye tracking.

The parameters can include any or any combination of a zoom feature, a microscope feature, magnifying feature, illumination feature; a retinal projection feature. In an embodiment a 360 degree view can be provided. The 360 degree view can be any or any combination of a left or right panning, up and down panning, three dimensional rotations.

In another embodiment, an illumination feature is directed to a specific area based upon the dynamic eyetracking mechanism. A wearable optics device camera feature can filter certain light waves for controlled viewing or visual effects. The filtering feature can include controlling noise reduction, polarization, and creative effects. The wearable optics device feature can include controlling a stability control for facial or object focus. In an embodiment optical parameters can be utilized. The optical parameters include any of or any combination of ciliary, pupil, corneal, retina, lens, iris measurements. An embodiment may include detecting head movement. An acoustic wave mechanism may be utilized within the wearable optics device. A brain wave mechanism may be utilized within the wearable optics device. A magnetic wave mechanism may be utilized within the wearable optics device.

The wearable optics device can be utilized in a variety environments including but not limited to athletic, gaming, gambling, educational, military, firefighting, medical dental, and the like. To describe the features of the present invention in more detail refer now to the following description in conjunction with the accompanying figures

FIG. 6

Figure 6:
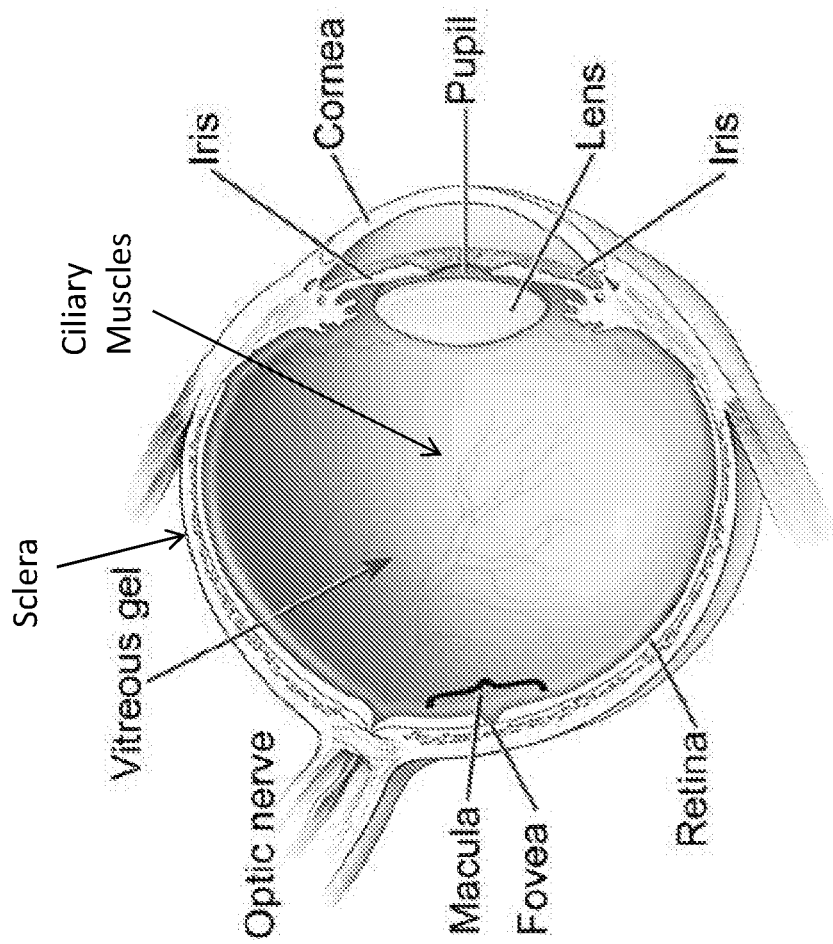
FIG. 6 illustrates the parts of an eye that may be utilized with the eye tracking mechanism of an embodiment.

FIG. 6 illustrates the parts of an eye that may be utilized with the eye tracking mechanism of an embodiment. In an embodiment, the iris, retina cornea, pupil, ciliary, and lens can all be utilized either singly or in combination to enable the dynamic eye tracking mechanism.

FIG. 7

Figure 7:
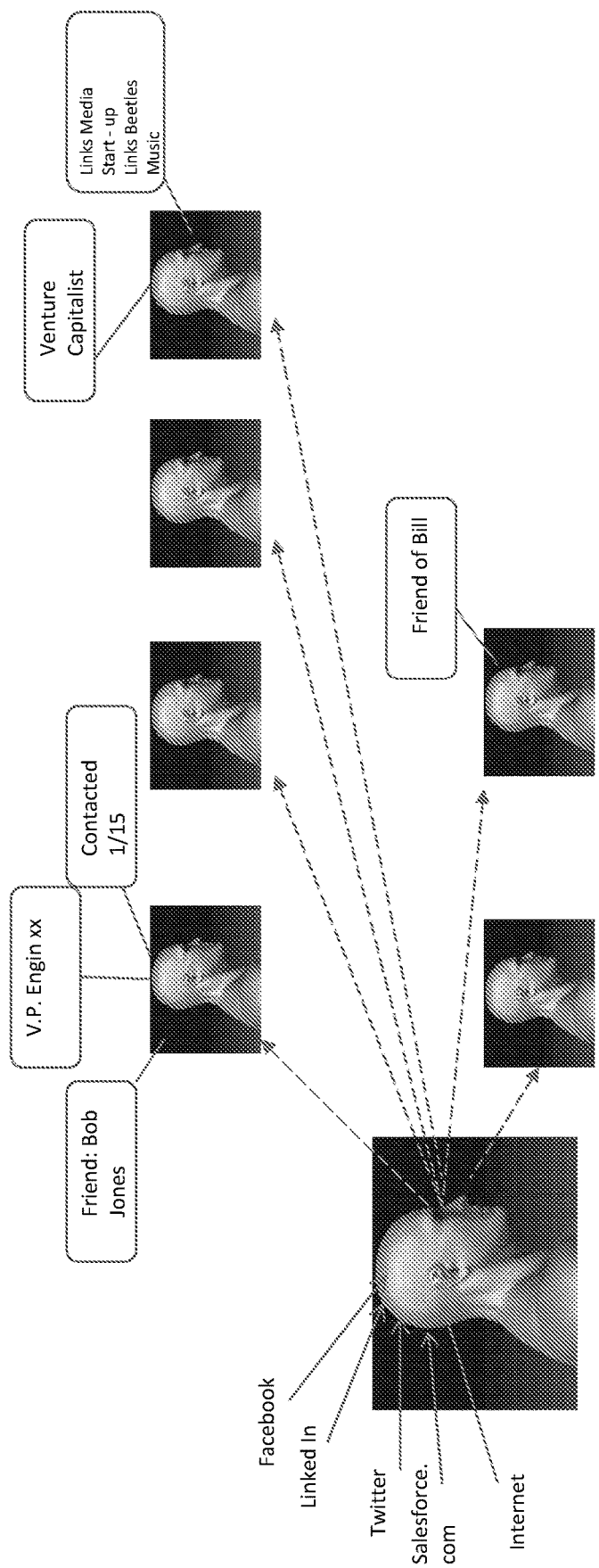
FIG. 7 illustrates a social networking application utilized with the wearable optics device.

Social networks can be leveraged advantageously with the wearable optics device in accordance with an embodiment. FIG. 7 illustrates a social networking application 700 utilized with the wearable optics device. The networks of Facebook, Linked In, Twitter, Salesforce.com, and other networks, as well as the Internet are connected to the wearable optics device.

Individuals that are "Friends" for example, can be identified by a highlight by the wearable optics device. Information about individuals can be gathered by using eyes utilized by the wearable optics device architecture. In an embodiment, the individual can be selected. The individual can be identified in a variety of ways for example using facial recognition, target individual information, GPS, RFID, NFC, optical information, voice recognition, and mobile location.

FIG. 8

Figure 8:
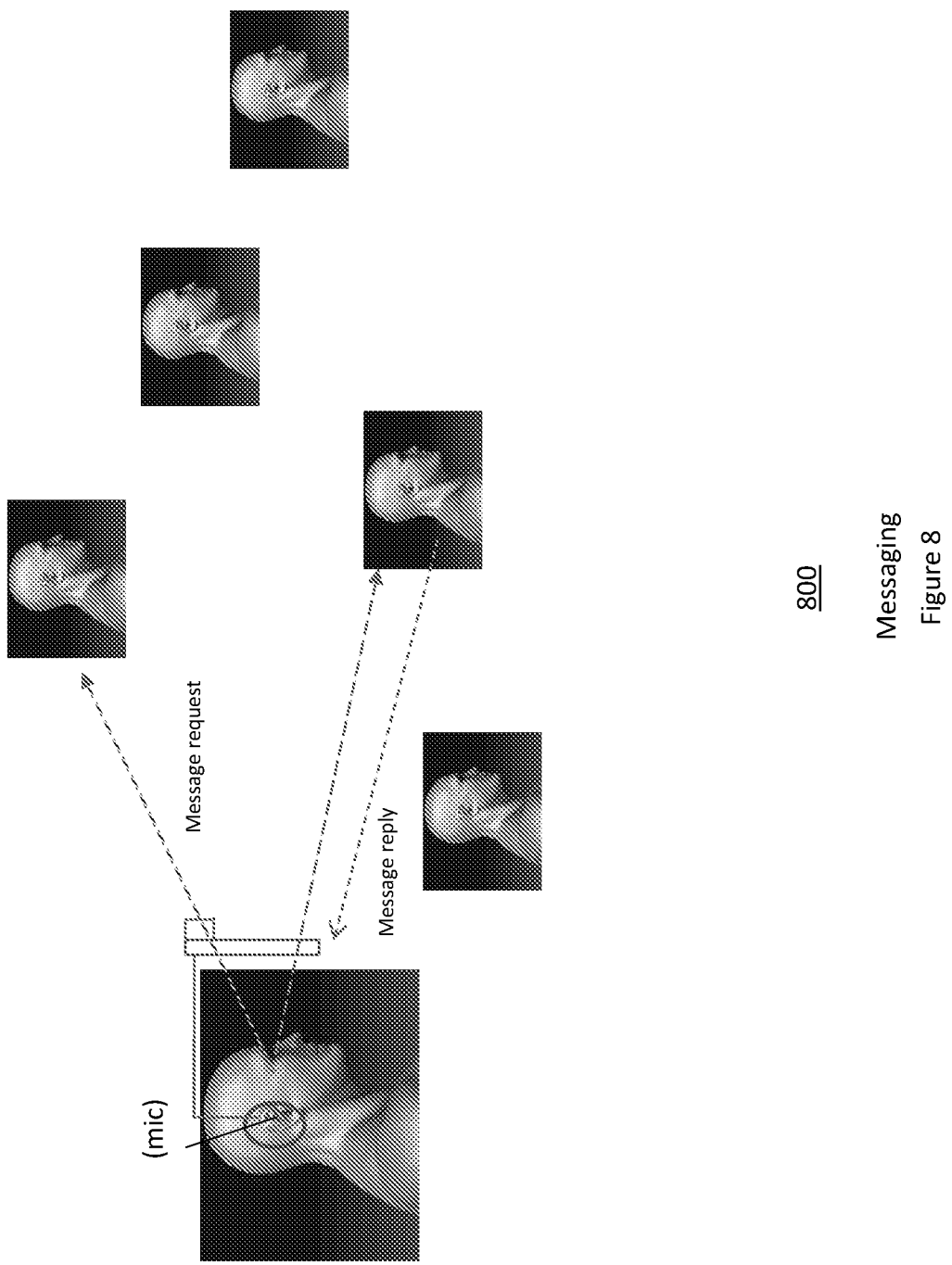
FIG. 8 illustrates a messaging application utilized with wearable optics device in accordance with an embodiment.

FIG. 8 illustrates a messaging application 800 utilized with wearable optics device in accordance with an embodiment. In this embodiment, information is transmitted via mobile, text, R2R, Internet, Wi-Fi, Facebook message, Twitter's tweet. The wearable optics device can utilize R2R, NFC, Wi-Fi, Internet to communicate. It is possible to talk using a microphone, sensors near the face, jaw, and nose can be utilized to provide control of the messaging application. In addition lip motion, and lip reading can be utilized to transmit voice in a silent and confidential manner. An individual can be targeted by using selected eye movements.

FIG. 9

Figure 9:
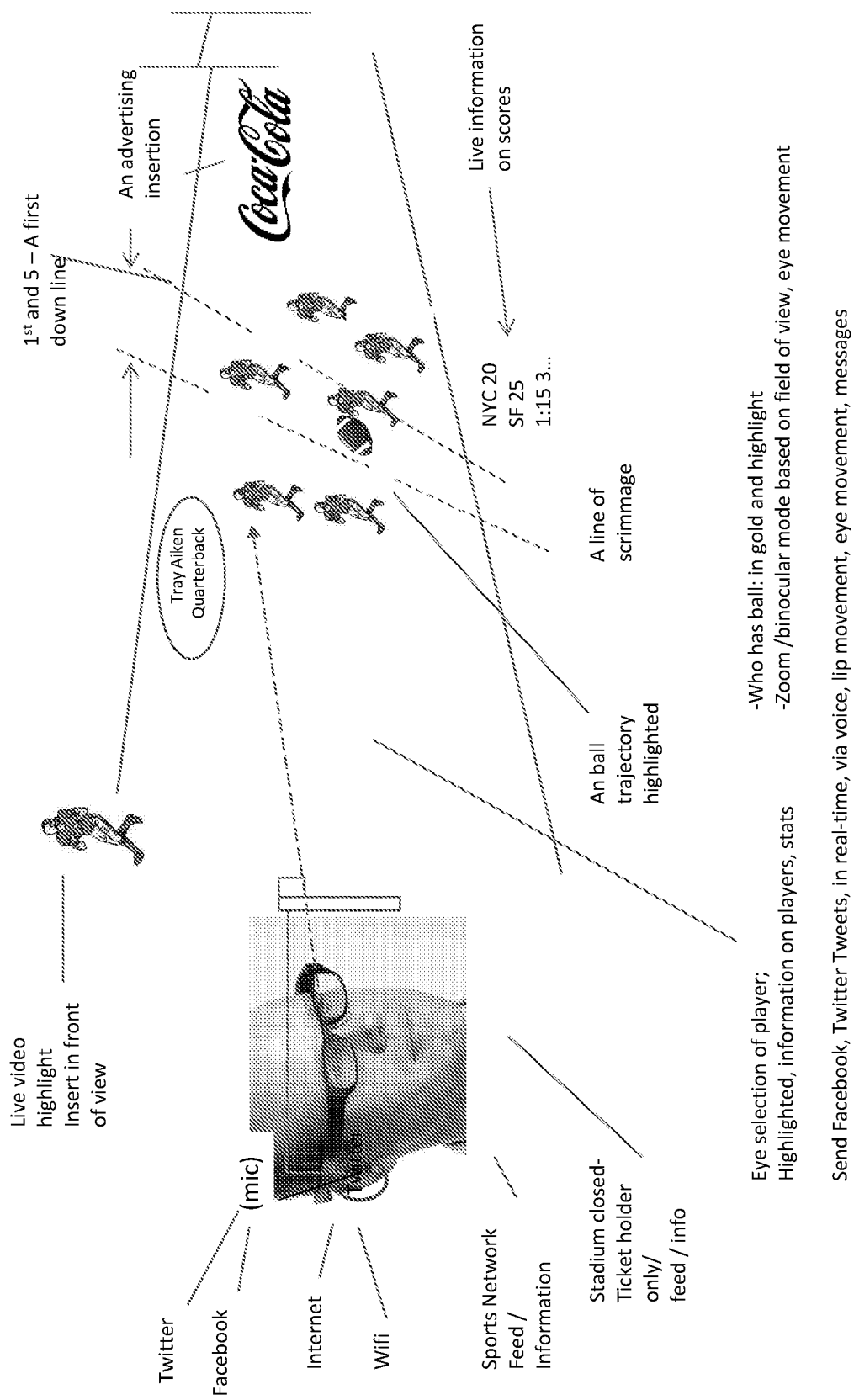
FIG. 9 illustrates the wearable optics device utilized by an athletic sports spectator in accordance with an embodiment.

FIG. 9 illustrates the wearable optics device utilized by an athletic sports spectator in accordance with an embodiment 900. Networks such as Twitter, Facebook, Internet are connected to the spectator. For example the spectator can see who has the ball and its course during a play. Who has the ball as well as the ball's location is highlighted. Video information can be overlayed from scores of other games. Information about the location of the football during the game (line of scrimmage, first down line). Video highlights of the game could be provided as well as augmented reality media.

FIG. 10

Figure 10:
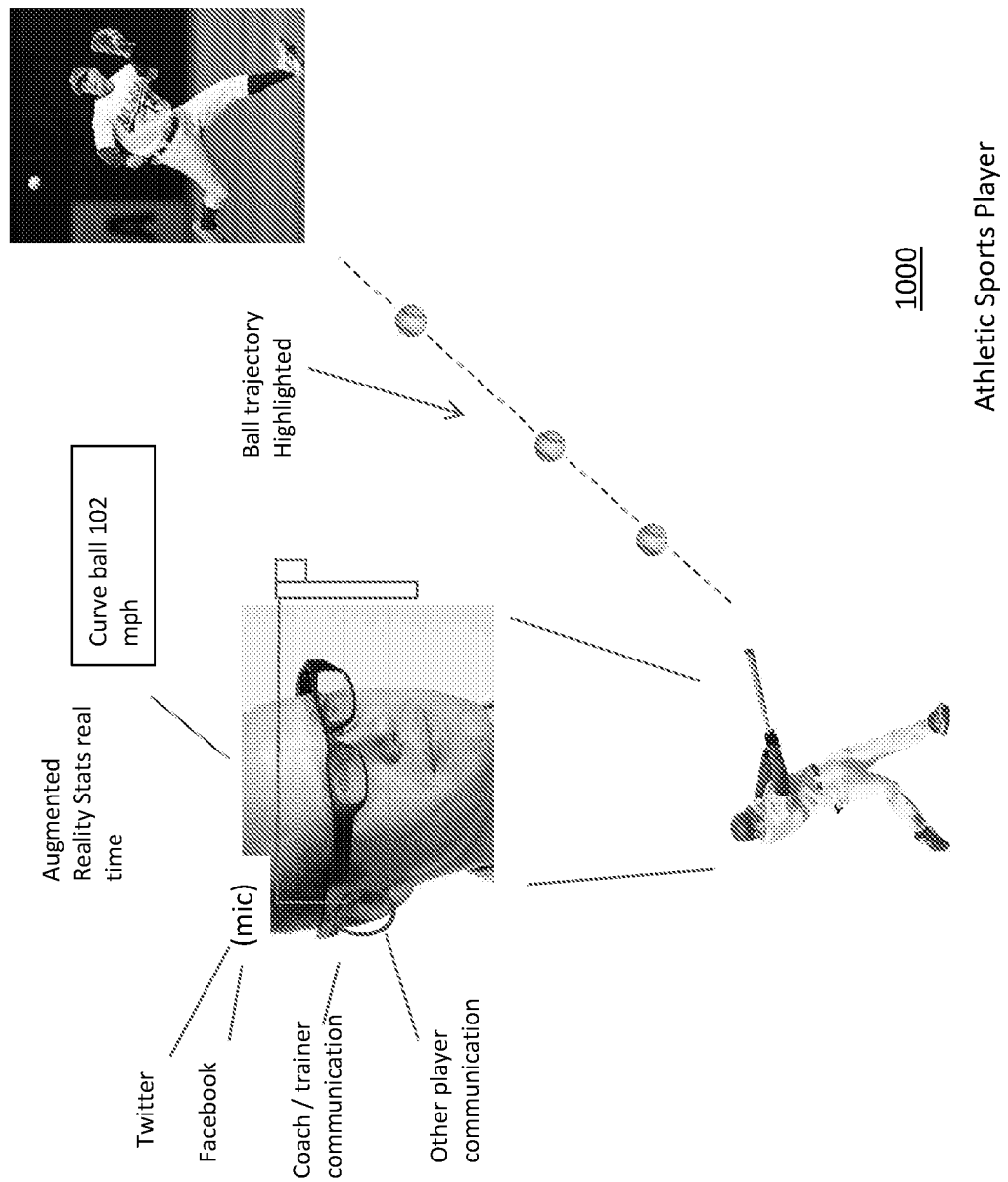
FIG. 10 illustrates the wearable optics device utilized by an athletic sports player in accordance with an embodiment.

FIG. 10 illustrates the wearable optics device utilized by an athletic sports player in accordance with an embodiment 1000. Networks such as Twitter, Facebook, Coach/trainer communication, and other player communications are connected to the player. For example the spectator can see that a curve ball is hit at 102 mph. The trajectory of the ball is highlighted.

FIG. 11

Figure 11:
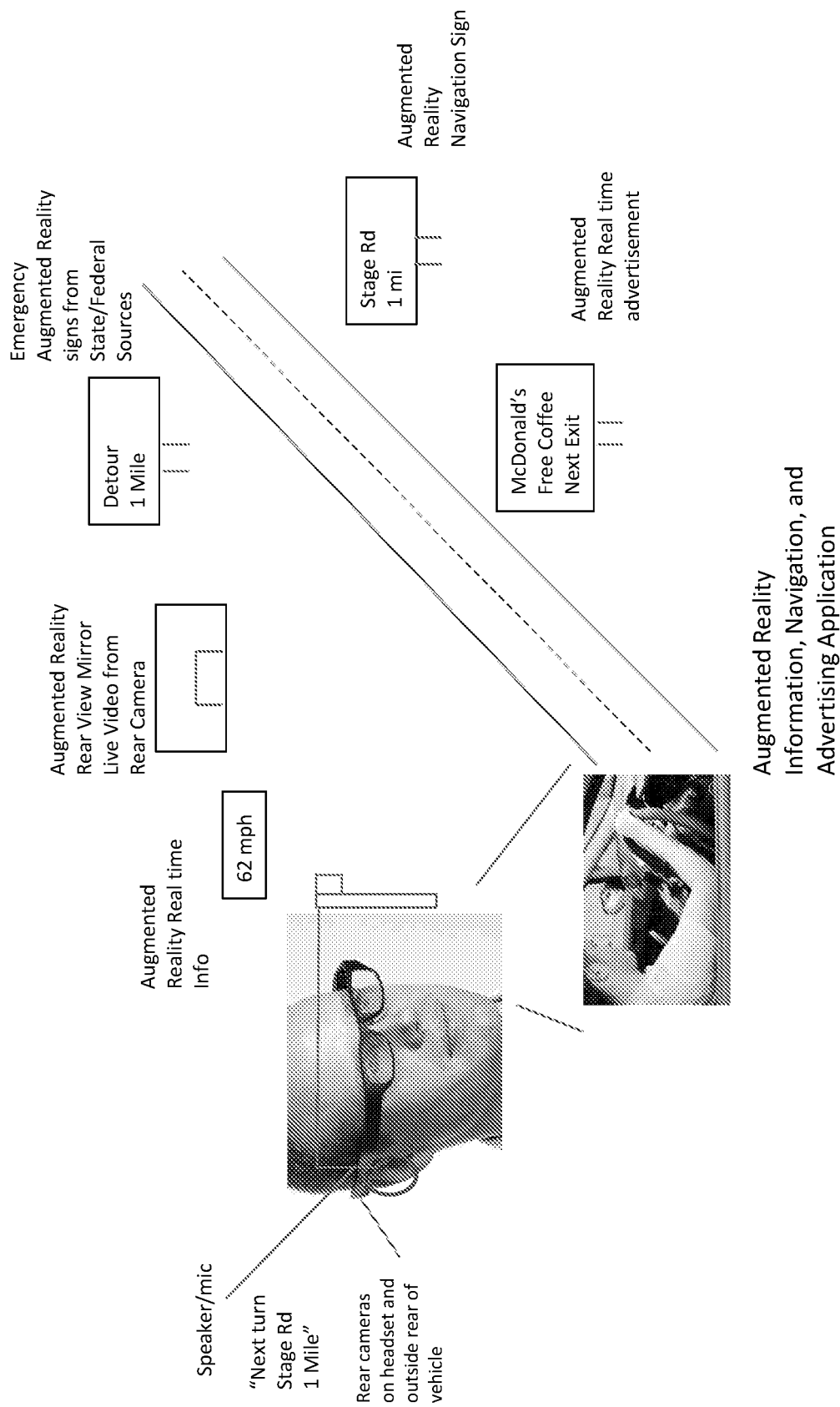
FIG. 11 illustrates an augmented reality information, navigation, and advertising application utilized with the wearable optics device.

FIG. 11 illustrates an augmented reality information, navigation, and advertising application 1100 utilized with the wearable optics device. In this embodiment, information is transmitted via mobile, text, R2R, Internet, Wi-Fi, Facebook message, Twitter's tweet. The wearable optics device can utilize mobile, R2R, NFC, Wi-Fi, Internet to communicate. In one example the wearable optics device is utilized in a vehicle. In this example the wearable optics device includes speaker microphone and rear camera on the headset and also on the rear of a vehicle for example. Augmented reality real time information is provided. For example, the Augmented Reality Real time information provided is that the vehicle is traveling at 62 mph.

There also may be Augmented Reality Mirror Live Video from Rear Camera of the car. For a sign that reads, "Detour 1 Mile" is shown on as an emergency Augmented Reality sign from State/Federal Sources which could also provide additional information.

In another example, "McDonald's Free Coffee" next exit, seen as an Augmented Reality real-time advertisement. "Stage Road 1 Mile", will also be seen as an Augmented Reality Sign while the voice message "Next turn Stage Rd. 1 mile" is transmitted to the driver together comprising an enhanced Augmented Reality GPS and navigation system.

FIG. 12

Figure 12:
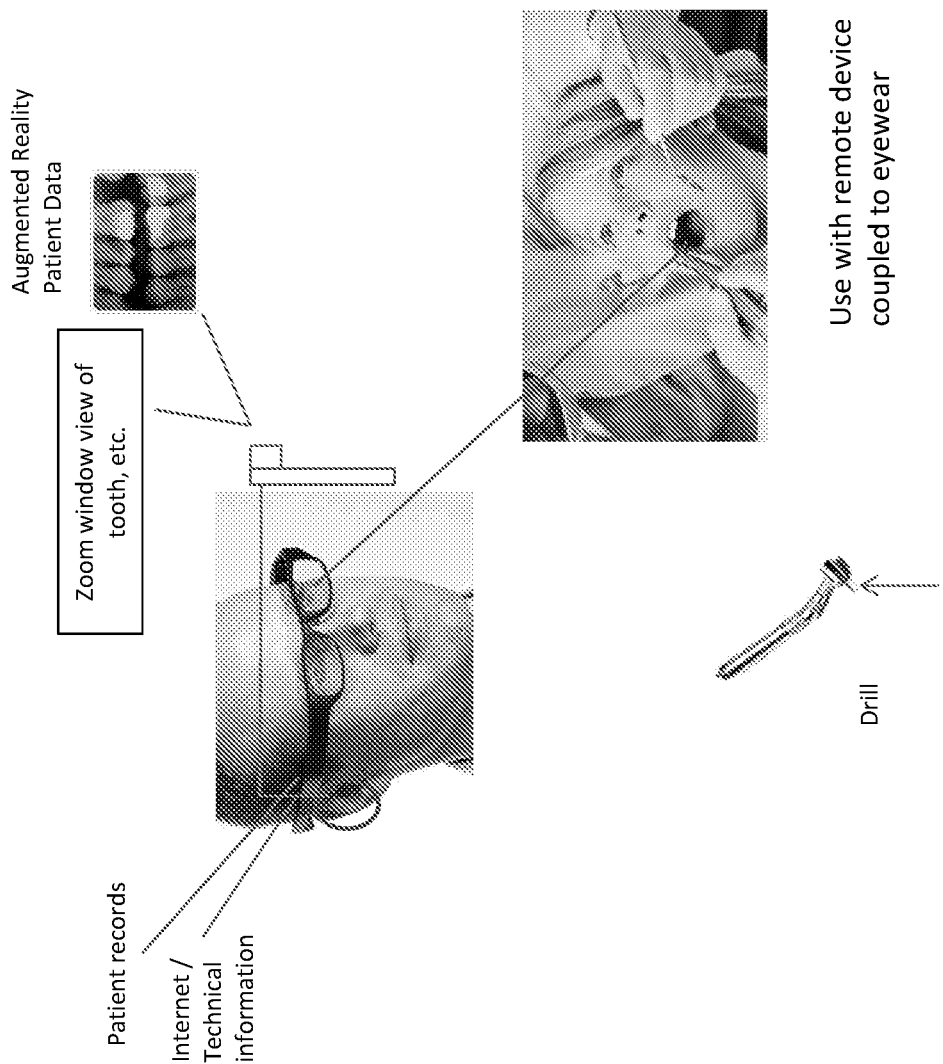
FIG. 12 illustrates an augmented reality information patient data application utilized with the wearable optics device used in conjunction with a remote device.

FIG. 12 illustrates an augmented reality information patient data application 1200 utilized with the wearable optics device used in conjunction with a remote device. In this embodiment, information is transmitted via mobile, text, R2R, Internet, Wi-Fi, Facebook message, Twitter's tweet. The wearable optics device can utilize mobile, R2R, NFC, Wi-Fi, Internet to communicate.

Patient records and internet technical information are connected to the eyepiece and microphone of the person who is utilizing the wearable optics device. Utilizes an augmented reality zoom window to identify medical feature. Augmented reality patient data is made available to the person via the eyewear. There may also be a remote device camera utilized on the drill of a dentist for example. The dentist for example can utilize the dynamic eye tracking mechanism to focus on the correct tooth.

An overlay of the x-ray of the tooth can be seen utilizing the augmented reality. An augmented reality overlay of dental records and Internet research in tooth treatment is available. Dentist can use a remote drill with augmented reality. Illumination and zoom can also be utilized with an augmented reality window.

FIG. 13

Figure 13:
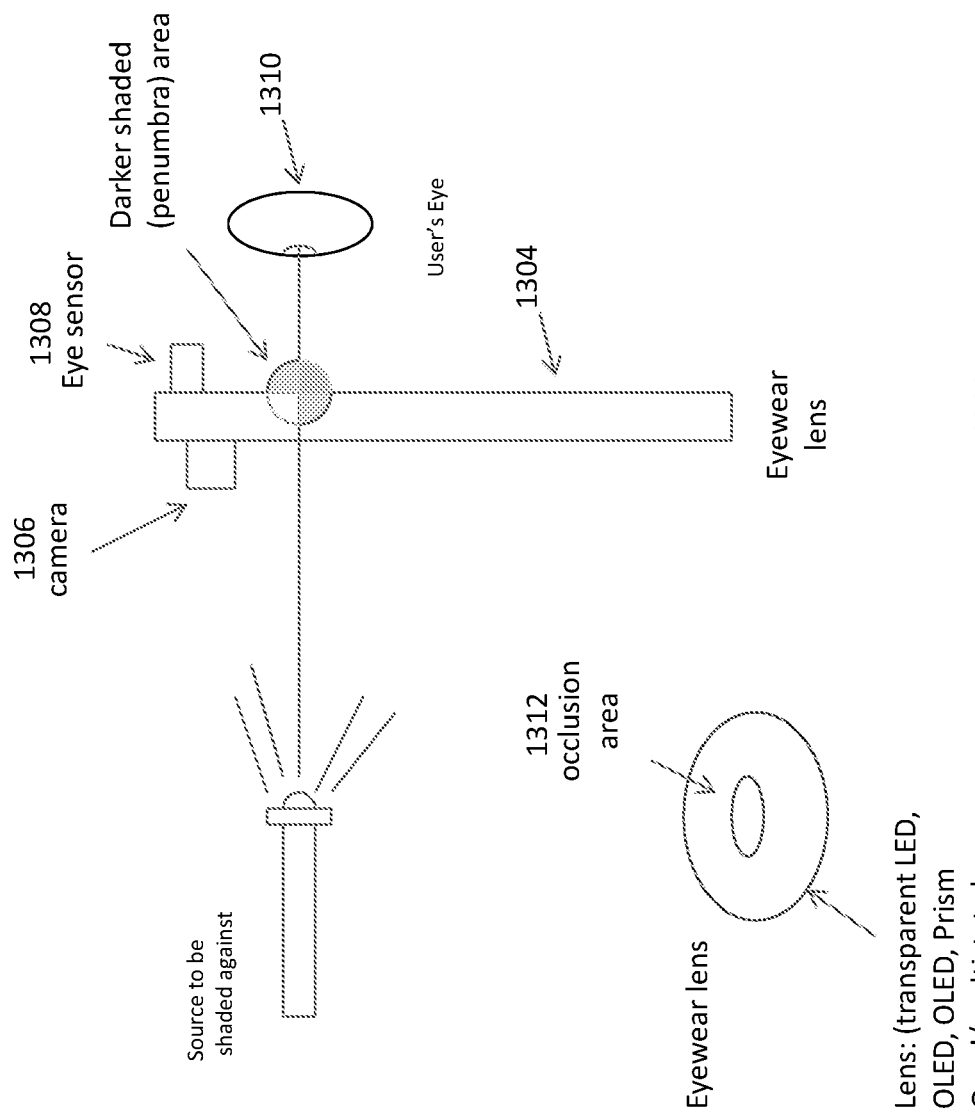
FIG. 13 illustrates a shading control application utilized with the wearable optics device.

FIG. 13 illustrates a shading control application 1300 utilized with the wearable optics device. In this embodiment, information is transmitted via mobile, text, R2R, Internet, Wi-Fi, Facebook message, Twitter's tweet. The wearable optics device can utilize mobile, R2R, NFC, Wi-Fi, Internet to communicate. Shading settings can be chosen through push buttons on the eyewear frame, via eye movement, or automatically. The shading can be uniform across the eyewear lens or concentrated in a specific area or areas of the lens.

In an embodiment a lamp/flashlight 1302 projects light to eye 1310. The camera 1306 and eye sensor 1308 pick up the light. The lens 1304 can be any or any combination of transparent LCD, LED, OLED, flexible LED, flexible OLED, transparent matrix, semi-transparent matrix, prism based, holographic, electroluminescence, eletroreflective, dynamic filtering materials.

Light can be occluded in a specific area 1312 utilizing the wearable optics device. The camera 1306 determines position of light to be occluded (real time). The eye sensor 1308 determines the position of the eye/pupil/retina (real time). The camera 1306/eye sensor 1308 determines line of sight between light to be occluded and eye 1310 and intersect area on lens 1304 (real time) or area to project occlusion from a projector embodiment.

FIG. 14

Figure 14:
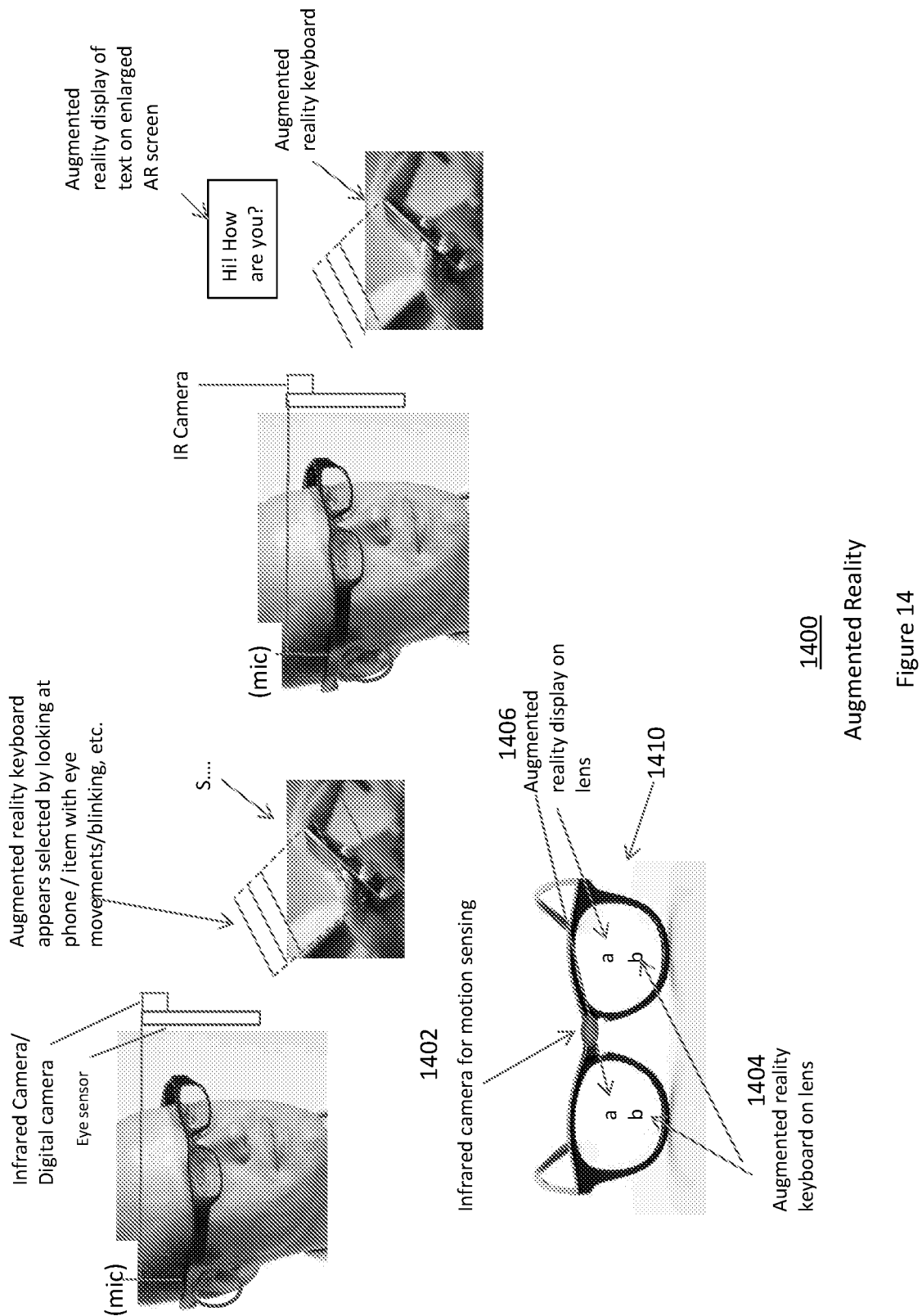
FIG. 14 illustrates an augmented reality application utilized with the wearable optics device.

FIG. 14 illustrates an augmented reality application 1400 utilized with the wearable optics device 1410. In this embodiment, information is transmitted via mobile, text, R2R, Internet, Wi-Fi, Facebook message, Twitter's tweet. The wearable optics device 1410 can utilize mobile, R2R, NFC, Wi-Fi, Internet to communicate.

In an embodiment, an augmented reality keyboard 1404 appears selected by look at the phone/item and then blinking or the like. The augmented reality (AR) keyboard 1404 is utilized that is controlled by the dynamic eye tracking mechanism. An infrared camera 1402 is used to sense the position of any of the user's hand, hand movement, finger position, finger movement on the AR keyboard such as key highlight and key click sound. There is an augmented reality display 1406 which is an enlargement of the small phone display, on the lens. There is also an augmented reality keyboard which is shown as being on the lens.

FIG. 15

Figure 15:
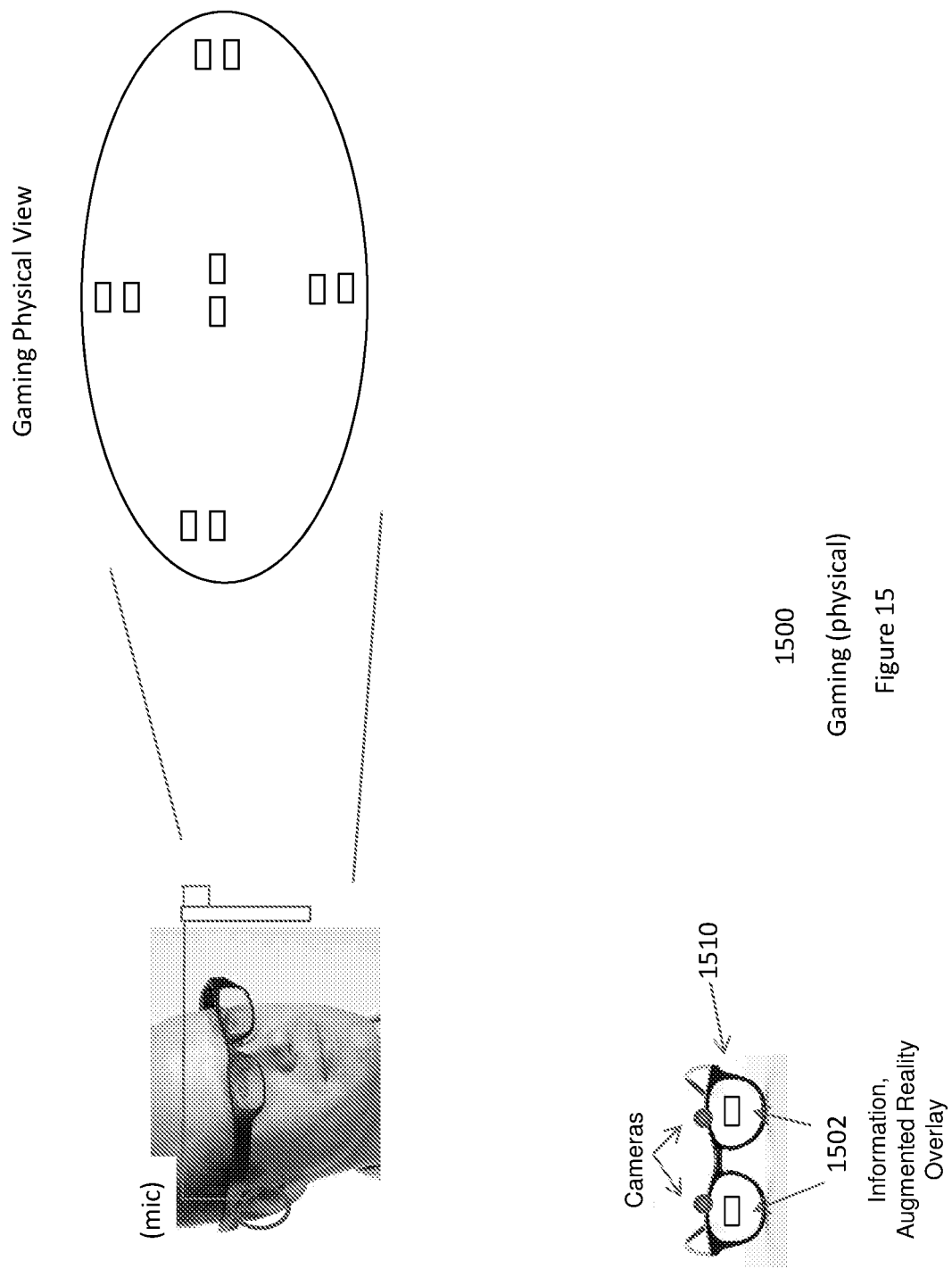
FIG. 15 illustrates a physical gaming application utilized with the wearable optics device.

FIG. 15 illustrates a physical gaming application 1500 utilized with the wearable optics device 1510. In this embodiment, information is transmitted via mobile, text, R2R, Internet, Wi-Fi, Facebook message, Twitter's tweet. The wearable optics device 1510 can utilize mobile, R2R, NFC, Wi-Fi, Internet to communicate.

In an embodiment, a person wearing the wearable optics device 1510 can analyze game strategy, count cards, determine the score, do analysis (of game statistics), and analyze other player's faces utilizing an augmented reality overlay 1502 and facial recognition.

FIG. 16

Figure 16:
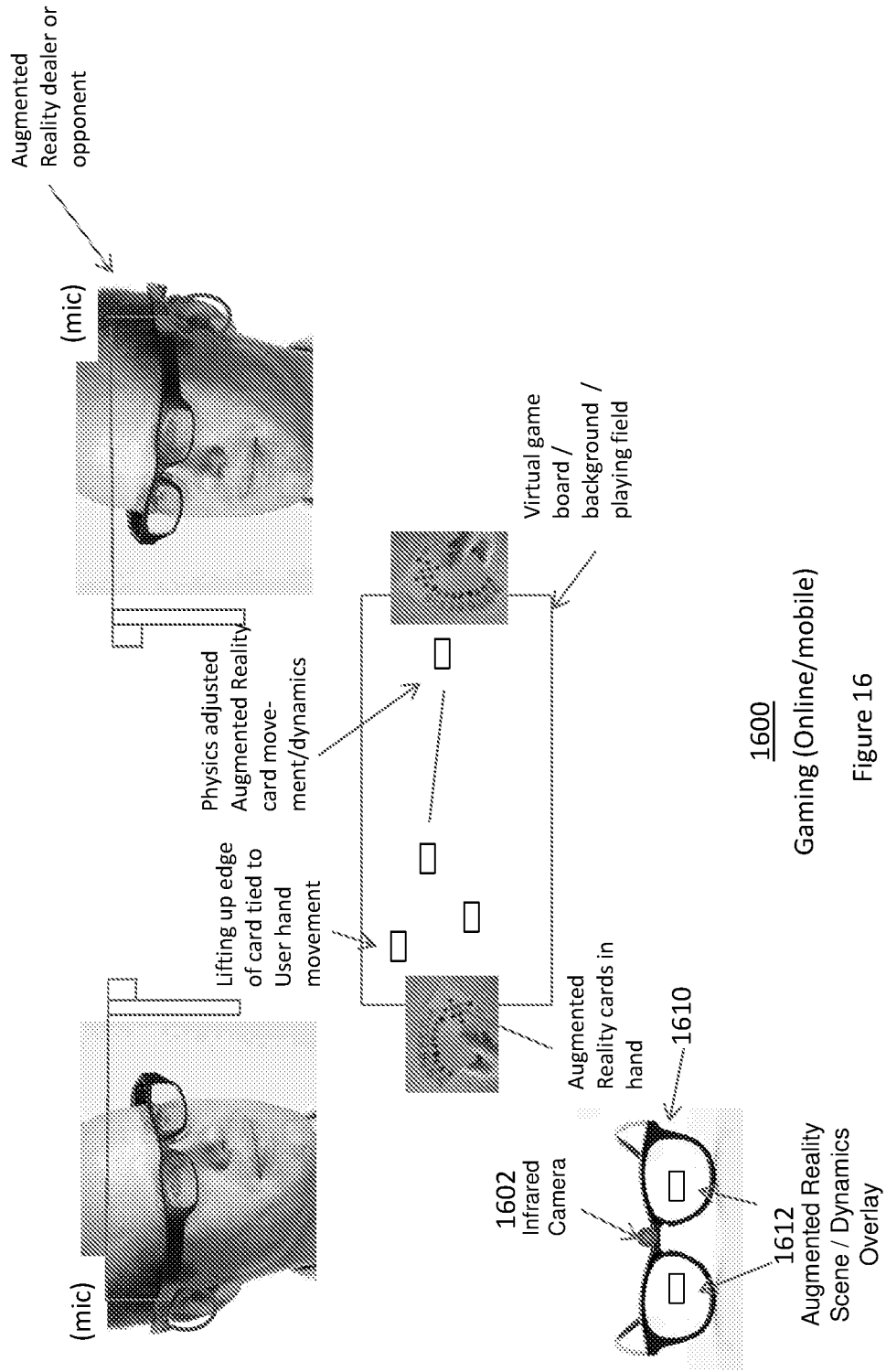
FIG. 16 illustrates a first embodiment of an online/mobile gaming application utilized with the wearable optics device.

FIG. 16 illustrates a first embodiment of an online/mobile gaming application 1600 utilized with the wearable optics device 1610. In this embodiment, information is transmitted via mobile, text, R2R, Internet, Wi-Fi, Facebook message, Twitter's tweet. The wearable optics device 1610 can utilize mobile, R2R, NFC, Wi-Fi, Internet to communicate.

The player and opponent have augmented reality cards in hand. Augmented reality playing cards are utilized. Because of the augmented reality and communication link the players need not be present in the same location. The AR cards may be lifted by hand movement. There is a physics adjusted augmented reality card movement and dynamics. In an embodiment there can be a virtual game board, a background, and a playing field.

There is an infrared camera 1602 on the glasses to measure and judge hand and finger position and movement. There is an augmented reality scene or dynamics overlay 1612 which can be seen on the lenses.

FIG. 17

Figure 17:
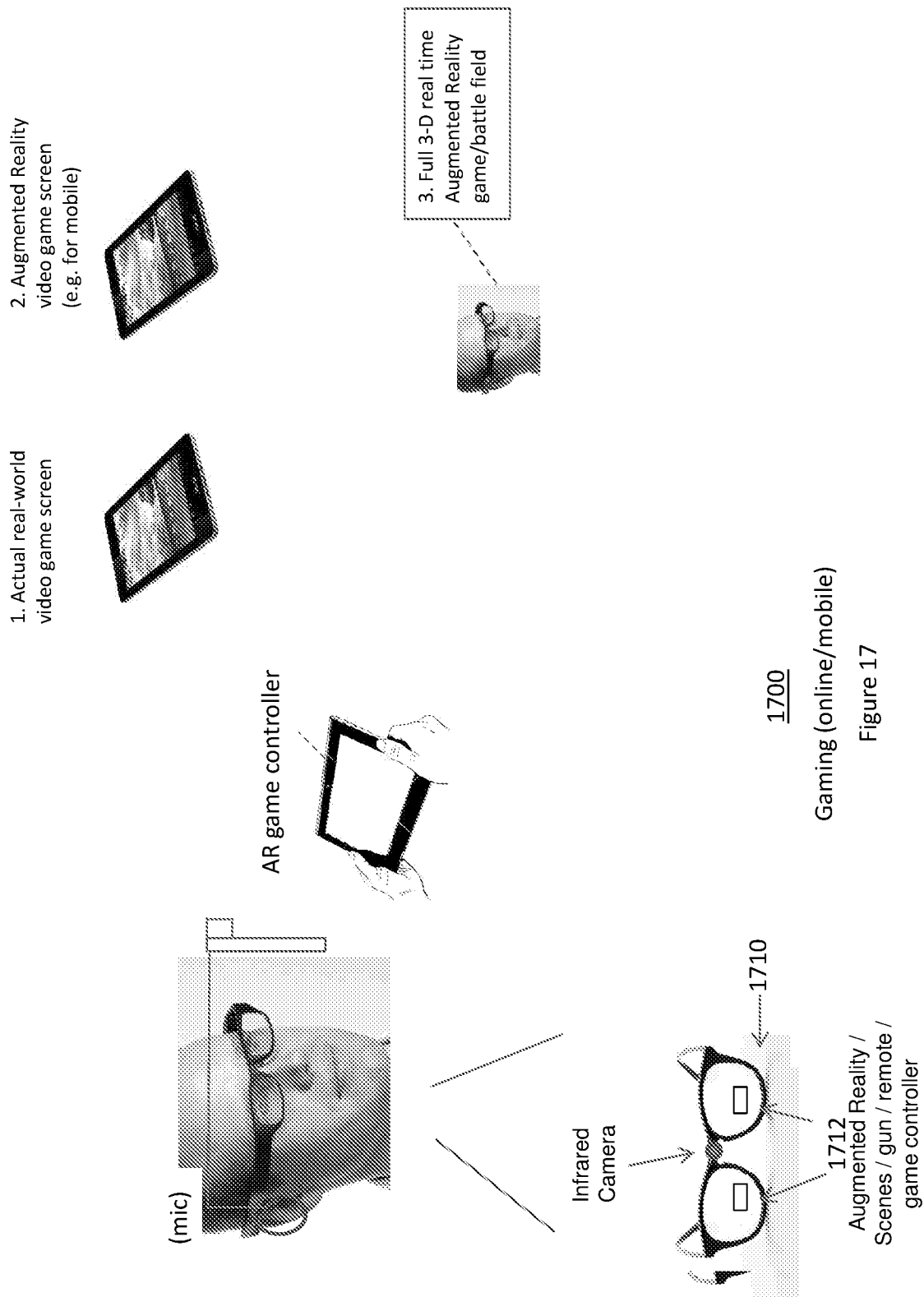
FIG. 17 illustrates a second embodiment of an online/mobile gaming application utilized with the wearable optics device.

FIG. 17 illustrates a second embodiment of an online/mobile gaming application 1700 utilized with the wearable optics device 1710. In this embodiment, information is transmitted via mobile, text, R2R, Internet, Wi-Fi, Facebook message, Twitter's tweet. The wearable optics device 1710 can utilize mobile, R2R, NFC, Wi-Fi, Internet to communicate.

The scene that the player sees can be an actual real-world video game screen. It could also be utilized as an augmented reality video game screen (e.g. for mobile). Furthermore it could also be utilized as a full 3-D real time Augmented Reality game/battle field which the player sees. The player can use an augmented reality game controller. There is an infrared camera on the glasses to measure and judge hand and finger position and movement on the AR game controller. Augmented reality scenes, AR game controller, AR gun, or AR remote control overlay 1712 are seen on the lenses of the glasses.

FIG. 18

Figure 18:
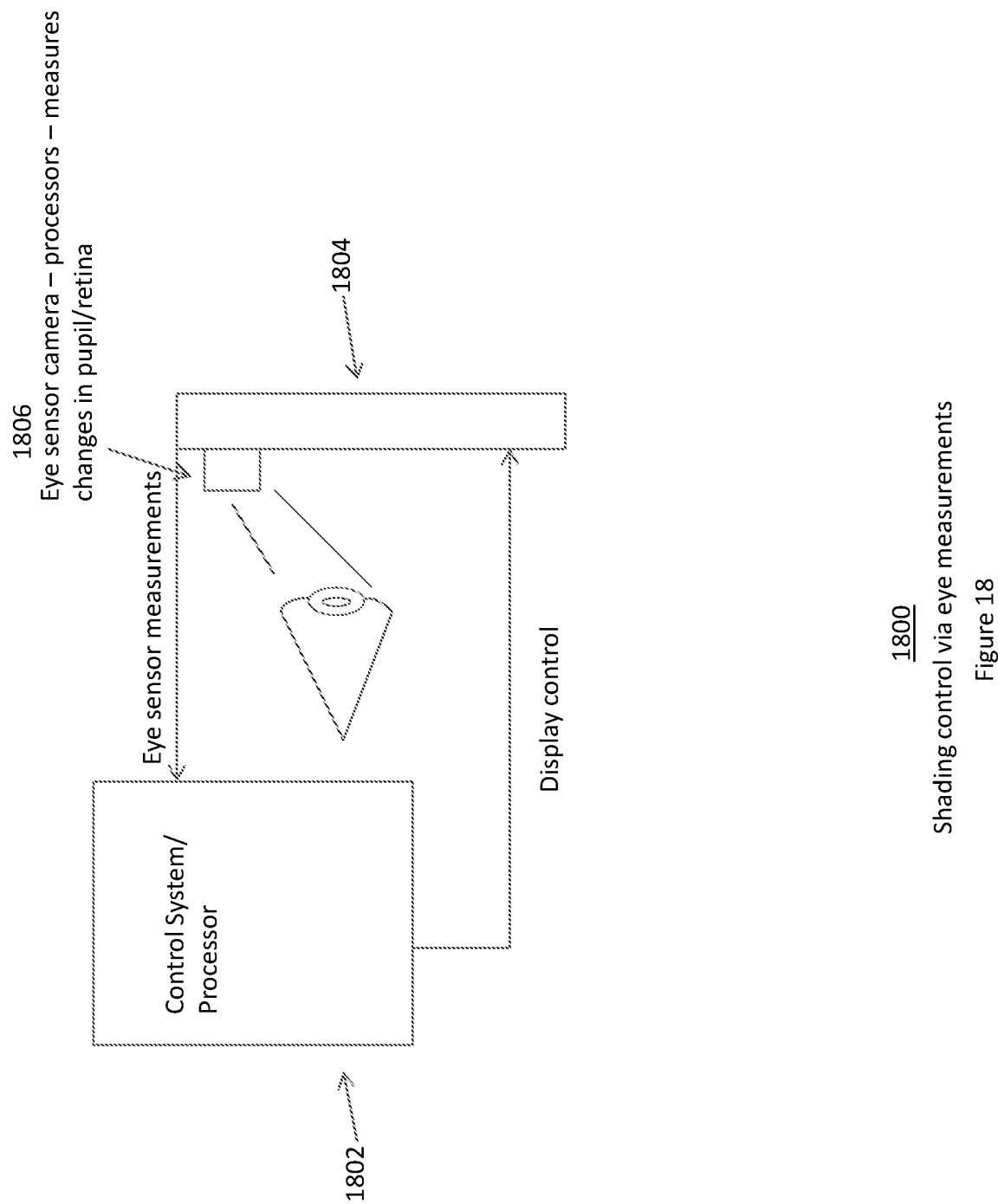
FIG. 18 illustrates shading control utilizing the wearable optics device.

FIG. 18 illustrates shading control mechanism utilizing the wearable optics device. In this embodiment there are one or more cameras 1806 that measures changes in the eye (for example the pupil or the retina) and sends the information to a processing system. Thereafter, the processing system 1802 can control a display on the lens 1804 to provide shading.

FIG. 19

Figure 19:
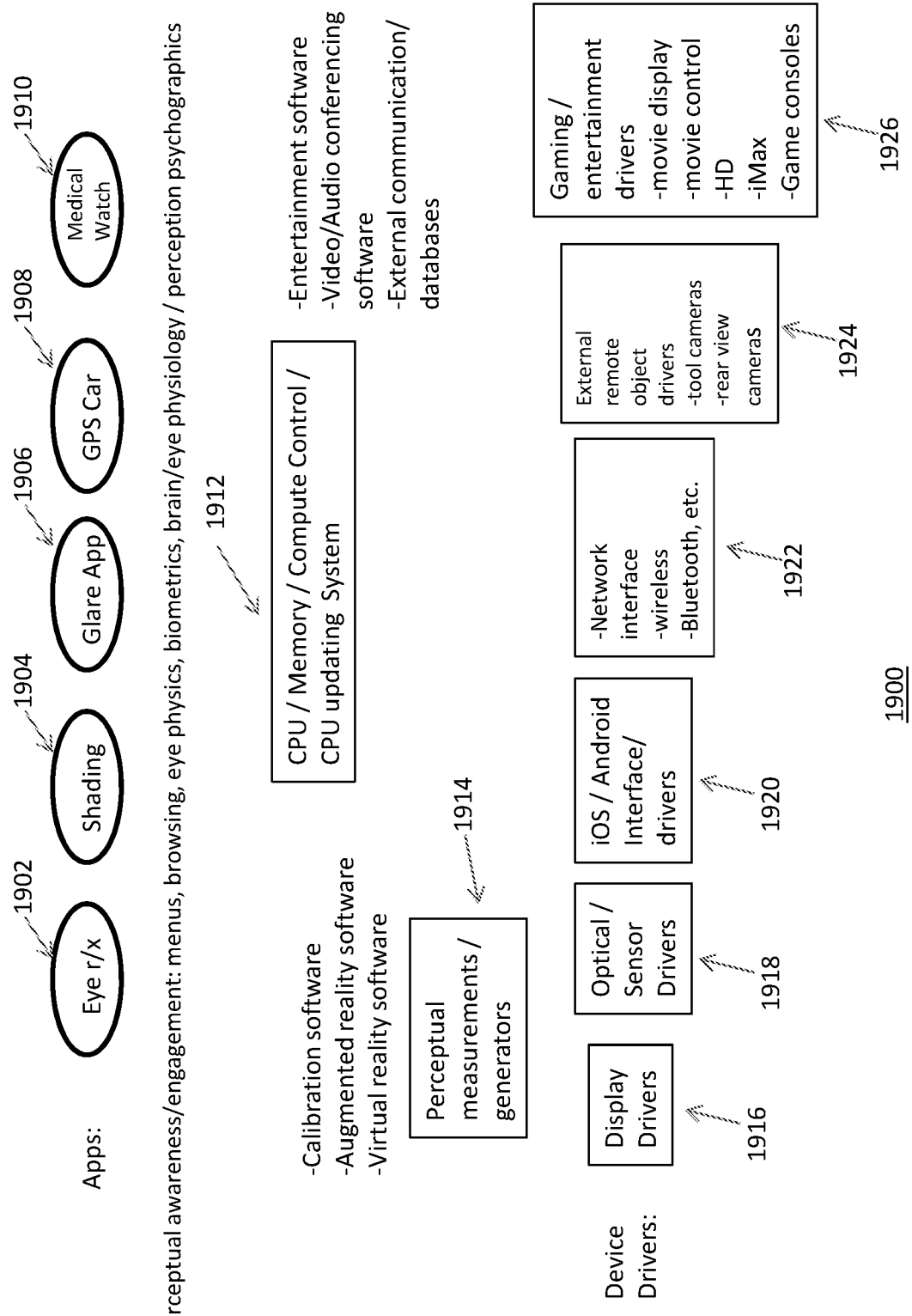
FIG. 19 illustrates an optical/perceptual operating system with the wearable optics device.

FIG. 19 illustrates an optical/perceptual operating system 1900 with the wearable optics device. As is seen a plurality of applications 1902-1910 interface with a processing system. The processing system includes a CPU, Memory, computer control and a CPU updating system 1912.

The applications include but are not limited to an eye prescription 1902, shading 1904, a glare application, 1906, GPS for navigation of a vehicle 1908 and a medical application 1910. The system would include perceptual measurement/generators 1914. These would include but are not limited to calibration software, augmented reality software, entertainment software, video/audio conferencing software and external communication/databases. The system would also include one or more device drivers. They include but are not limited to display drivers 1916, optical/sensor drivers 1918, operating system drivers 1920, network drivers 1922, external remote object drivers 1924 and gaming/entertainment drivers 1926.

FIG. 20

Figure 20:
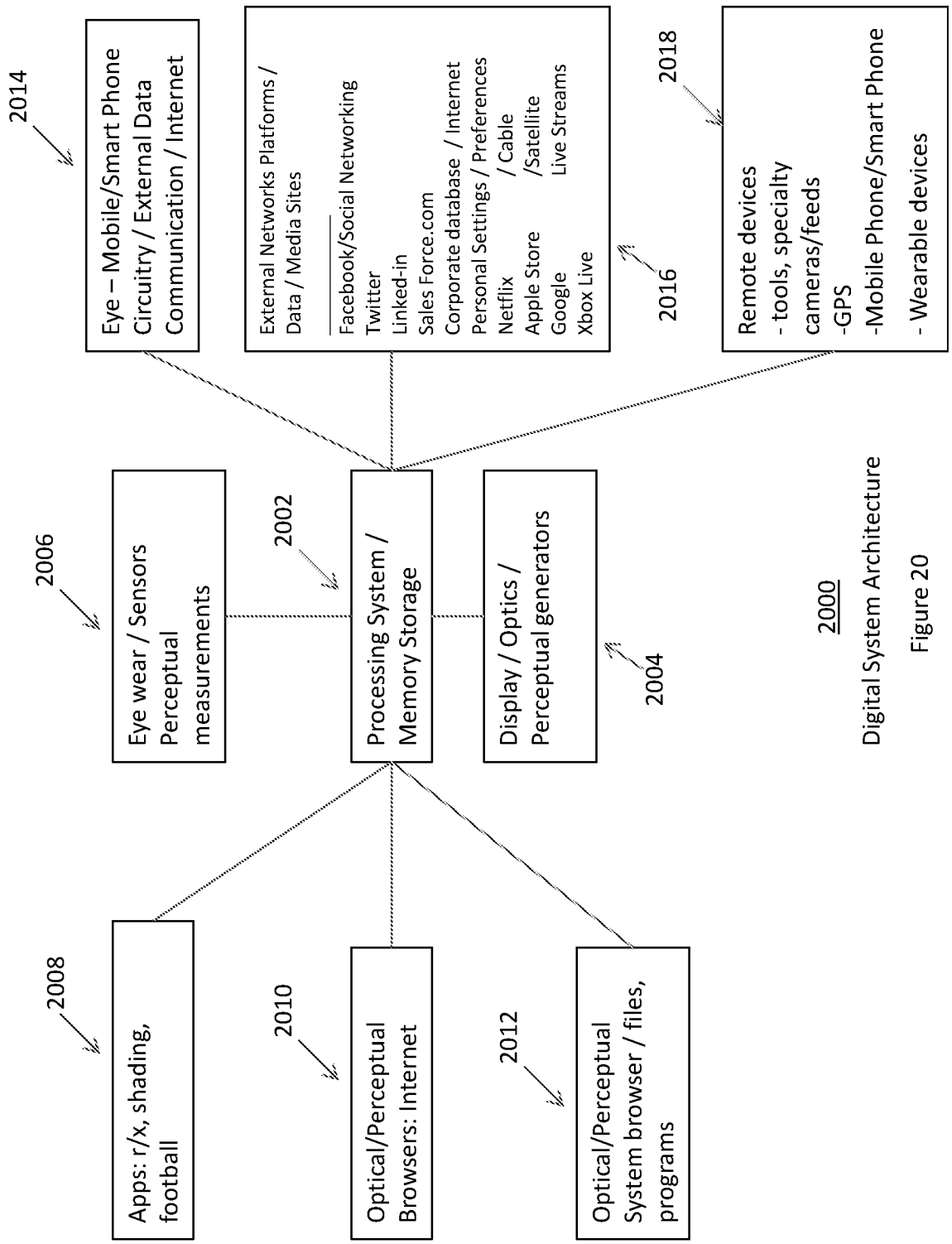
FIG. 20 describes an embodiment of the digital architecture of the wearable optics device.

FIG. 20 describes an embodiment of the digital architecture of a wearable optics device 2000. In this embodiment, the wearable optics device eyewear includes mobile/smart phone circuitry/external data communication/and circuitry for transmitting data via mobile, text, R2R, Internet, Wi-Fi, Facebook message, Twitter's tweet, along with networking to external networks platforms/data/media sites 2016. The wearable optics contains a processing system 2002 with memory storage, sensors for optical and perceptual measurement 2006, circuitry to control the optical display and perceptual generation needs of the device 2004, and interface 2008 to remote devices such as tools, specialty camera, GPS, mobile phone, wearable devices and the like.

In this embodiment various types of application software ("apps") 2018 can be run on the wearable optics device 2000 including shading control applications, focus and user eye adjustment prescriptions, and augmented reality applications for games such as football. An Internet browser 2010 that utilizes optical or perceptual parameters to drive navigation of the Internet can be used such that eye movements or facial expressions can accelerate the browsing process to the desired information. The wearable optics device 2000 contains a system browser 2012 with file storage that can be on the device or accessed via one of the networks to the device.

The device 2000 can be powered by a separate battery (not shown). The battery can be charged via a connector, such as but not limited to an USB connector to a charging device laptop, tablet or desktop PC for example. In addition the device 200 could be solar powered either by solar cells being placed on the device 2000 or the solar cells could be placed on articles of clothing (i.e. hat, shirt or pants for example) to facilitate the charging thereof.

FIG. 21

Figure 21:
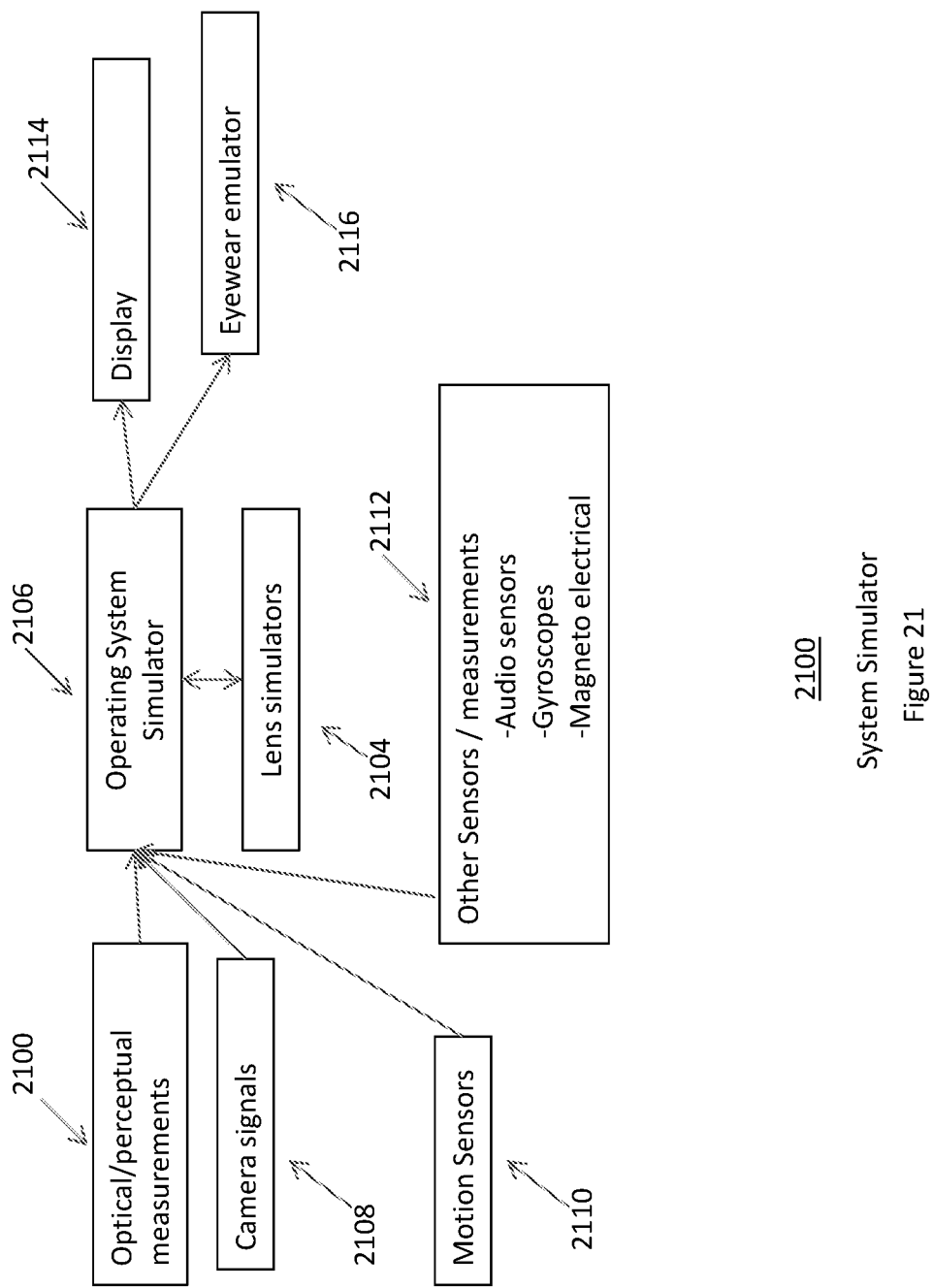
FIG. 21 illustrates the embodiment of a system simulator for use by developers of applications and new lenses or expansion of the wearable optics device.

FIG. 21 illustrates the embodiment of a system simulator 2100 for use by developers of applications and new lenses or expansion of the wearable optics device. In this embodiment, there is a simulator for the operating system 2102, a lens simulator 2104, a display 2114, and an eyewear emulator 2116. Optical/perceptual measurements 2106, camera signals, and other sensors and measurements are inputs to the simulator. The developer apps or new lenses can then be tested for various types of wearable options with various types of operating systems including iOS, Andriod, and general purpose or optimized optical/perceptual operating systems.

FIG. 22A-22F

Figures 22A, 22B:
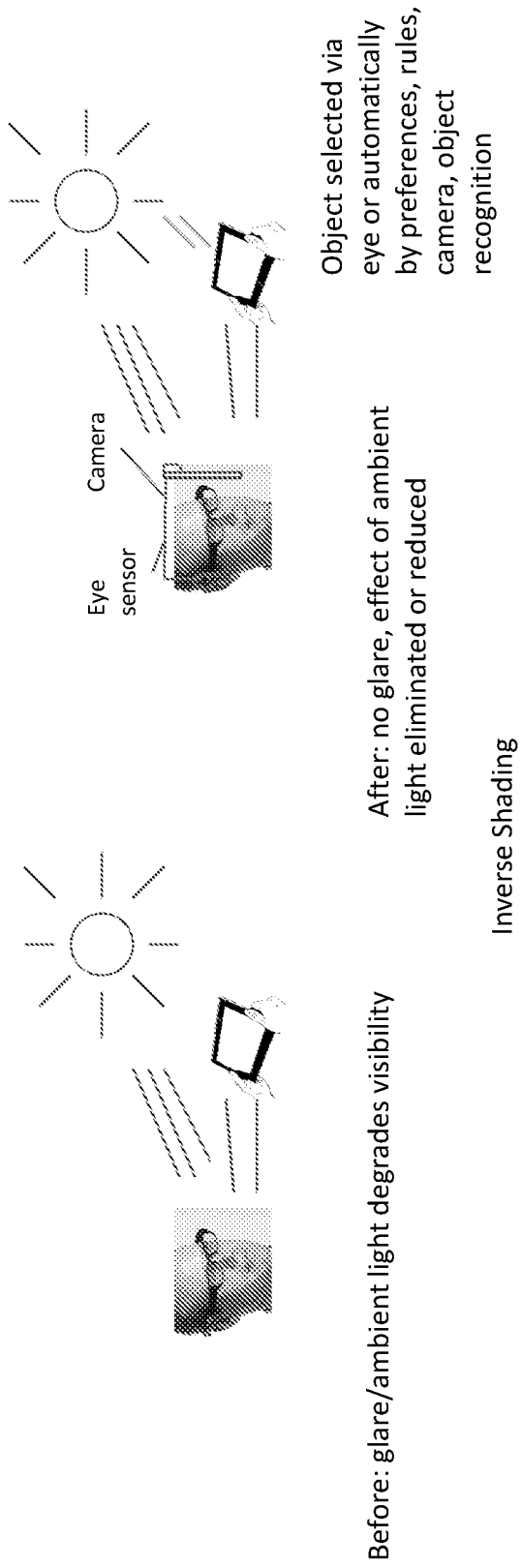

FIG. 22A through FIG. 22F illustrate an embodiment of inverse shading using the wearable optics device. FIG. 22A illustrates the problem of glare caused by ambient light which degrades the visibility of a object such as the screen of a mobile phone or laptop. FIG. 22C describes the iris/pupil contraction due to brightness which degrades retina/cornea and brain view of target object such as a phone screen or the like. In FIG. 22E the phone screen appears dark since ambient light is far brighter than screen.

FIG. 22B illustrates the selection of the target object as in a phone screen via eye or automatically by preferences, rules, camera image capture and object recognition. FIG. 22D shows eye detection and capture of the object's position and image by a camera on the eyewear. FIG. 22F shows the resulting elimination or reduction in glare and increase in visibility of the object wherein a shaded or translucent background follows surrounding area object in real time as seen from the user of the wearable optics device.

FIG. 23

Figure 23:
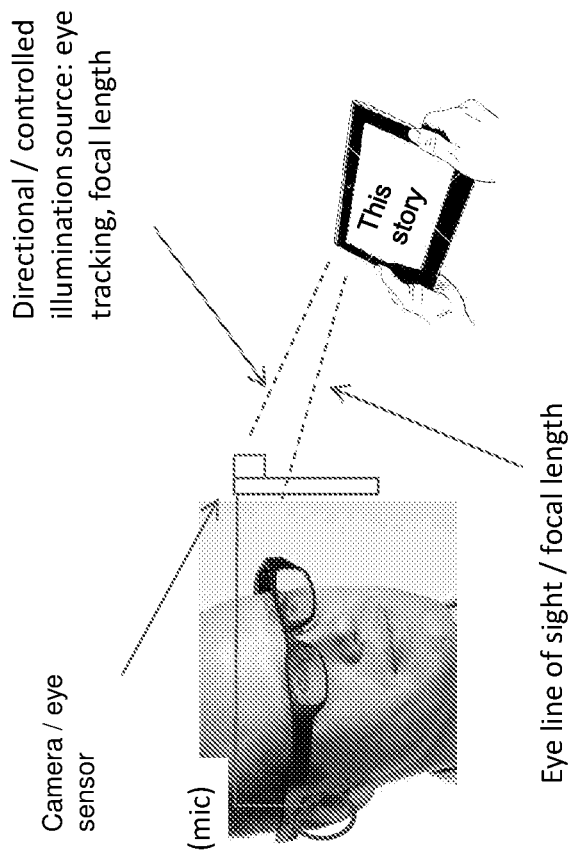
FIG. 23 illustrates an embodiment of eye tracking illumination and enhanced efficiency utilizing the wearable optics device.

FIG. 23 illustrates an embodiment of eye tracking illumination and enhanced efficiency utilizing the wearable optics device. Using the eye sensor and camera the line of sight and focal length can be determined and used to control a directional illumination source such that the illumination source illuminates the area corresponding to the area being focused on by the user of the wearable optics device

FIG. 24

Figure 24:
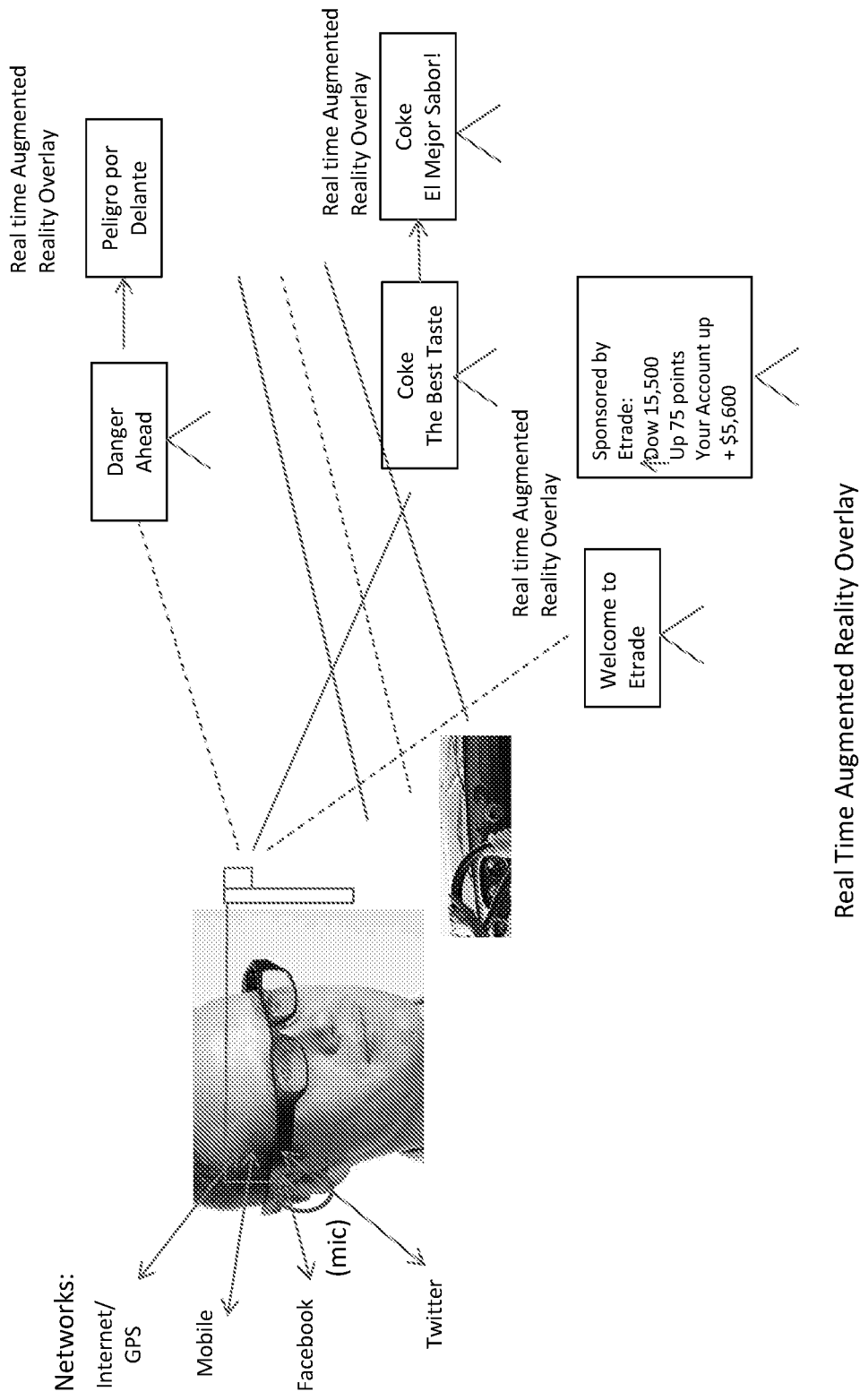
FIG. 24 illustrates an embodiment of real-time augmented reality overlay utilizing the wearable optics device.

FIG. 24 illustrates an embodiment of real-time augmented reality overlay 2400 utilizing the wearable optics device. In this embodiment, information is transmitted via mobile, text, R2R, Internet, Wi-Fi, Facebook message, Twitter's tweet. The wearable optics device can utilize mobile, R2R, NFC, Wi-Fi, Internet to communicate. In one example the wearable optics device is utilized in a vehicle. In this example the driver's eyewear uses augmented reality to overlay advertising signs, which can be personalized to the user which appear as if they are normal roadside billboards. In this example a real-time updated augmented reality danger sign is posted before a road hazard with the augmented reality sign being generated in real-time using information from the networks connected to the wearable eyewear device. This example also shows real-time translation from English to Spanish of navigational warning and advertising signs using augmented reality with the wearable optics device.

Accordingly systems and methods in accordance with embodiments are disclosed that provide these enhanced features for wearable optics devices. To describe these features and embodiments in more detail refer now to the following description in conjunction with the following discussion. A key feature associated with these enhancements is providing a variety of perceptual parameters that can be utilized with the wearable optics devices. Examples of perceptual parameters include but are not limited to optical expression, voice, brain wave, environmental, audio, video, navigational, augmented reality, algorithmic, spatial, cognitive, interpretive.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

The invention claimed is:

1. A wearable optics device comprising:
a lens; and
a dynamic eye tracking mechanism in communication with the lens;
wherein the dynamic eye tracking mechanism utilizes optical parameter measurements;
wherein the optical parameter measurements include one or more of:
ciliary measurements, pupil measurements, corneal measurements, iris measurements, eye lens measurements, eye lid measurements, or retina measurements;
one or more camera components and one or more communication components connected to the dynamic eye tracking mechanism;
wherein the lens projects an augmented reality overlay to a real world game within the view of a user based on the dynamic eye tracking mechanism inputted from the one or more camera components and the one or more communication components.

2. The wearable optics device of claim 1,
including one or more of
a zoom feature, a microscope feature, a magnifying feature, an illumination feature, a retinal projection feature, or a 360 degree view feature.

3. The wearable optics device of claim 2,
wherein the 360 degree feature comprises one or more of
a left or right panning feature, an up and down panning feature, or a three dimensional rotation feature.

4. The wearable optics device of claim 2,
wherein augmented reality is provided.

5. A wearable optics device, including
a lens; and
a dynamic eye tracking mechanism in communication with the lens;
wherein the dynamic eye tracking mechanism utilizes optical parameter measurements;
wherein the optical parameter measurements include one or more of ciliary measurements, pupil measurements, corneal measurements, iris measurements, eye lid measurements, or retina measurements;
wherein the dynamic eye tracking mechanism provides parameters personalized to a user based on the optical parameter measurements;
wherein the parameters personalized to the user include one or more of
a zoom feature, a microscope feature, a magnifying feature, an illumination feature, a retinal project feature; or a 360 degree view feature, one or more camera components and one or more communication components connected to the dynamic eye tracking mechanism;
wherein the lens projects an augmented reality overlay to a real world game within the view of a user based on the personalized parameters and the dynamic eye tracking mechanism inputted from the one or more camera components and the one or more sensors.

6. The wearable optics device as in claim 5,
wherein the 360 degree feature comprises one or more of
a left or right panning feature, an up and down panning feature, or a three dimensional rotation feature.

7. A wearable optics device, including
a lens; and
a dynamic eye tracking mechanism in communication with the lens;
wherein the dynamic eye tracking mechanism utilizes optical parameter measurements;
wherein the optical parameter measurements include one or more of
ciliary measurements, pupil measurements, corneal measurements, iris measurements, eye lid measurements, or retina measurements;
wherein the dynamic eye tracking mechanism provides parameters personalized to a user based on the optical parameter measurements;
wherein an illumination feature is directed to a specific area in response to the dynamic eye tracking mechanism wherein the illumination feature determined by using one or more camera components and one or more sensors connected to the dynamic eye tracking mechanism;
wherein the lens projects an augmented reality overlay to a real world game within the view of a user based on the personalized parameters and the dynamic eye tracking mechanism inputted from the one or more camera components and the one or more sensors.

8. The wearable optics device as in claim 7,
wherein the illumination feature includes controlling one or more of
a noise reduction feature, a polarization feature, a creative effects feature.

9. The wearable optics device as in claim 8,
wherein the illumination feature include controlling a stability control for at least one of facial or object focus.

10. A wearable optics device, including,
a lens; and
a dynamic eye tracking mechanism in communication with the lens;
wherein the dynamic eye tracking mechanism utilizes optical paramenter measurements;
wherein the optical parameter measurements include one or more of ciliary measurements, pupil measurements, corneal measurements, iris measurements, eye lid measurements, or retina measurements;
wherein the dynamic eye tracking mechanism provides parameters personalized to a user based on the optical parameter measurements;
sensory inputs are provided utilizing one or more sensors wherein the one or more sensors connected to the dynamic eye tracking mechanism;
wherein the lens projects an augmented reality overlay to a real world game within the view of a user based on the personalized parameters and the dynamic eye tracking mechanism inputted from the one or more sensors.

11. The wearable optics device as in claim 10,
wherein the sensory inputs are coupled to at least one of the one or more sensors.

12. The wearable optics device as in claim 10,
wherein the sensors include one or more of
a gyroscope, an accelerometer, a torque sensor, a weight sensor, a pressure sensor, a magnetometer, a temperature sensor, a light sensor, one or more cameras or microphones, a GPS sensor, a wireless detection sensor, an altitude senor, a blood pressure sensor, a heart rate sensor, a biometric sensor, a radio frequency identifier (RFID), a near field communication (NFC) device, a mobile communication device, a Wi-Fi device, a strain gauge, a fingerprint sensor, a smell sensor, a gas sensor, a chemical sensor, a color sensor, a sound sensor, an acoustic sensor, an ultraviolet sensor, an electric field sensor, a magnetic field sensor, a gravity sensor, a wind speed sensor, a wind direction sensor, a compass sensor, a geo-locator sensor, a polarized light sensor, or an infrared emitter sensor.

13. The wearable optics device as in claim 10,
Wherein the sensors are coupled wirelessly.

14. The wearable optics device as in claim 10,
wherein the sensors are coupled using one or more of
a USB wireless connection, or a Bluetooth wireless connection.

15. The wearable optics device as in claim 10,
wherein at least one of the sensors includes an earpiece coupled using one or more of
by a wire, to a frame, or using a wireless connection.

16. The wearable optics device as in claim 15,
wherein the earpiece includes ear muscle measurement.

17. The wearable optics device as in claim 16,
wherein the ear muscle measurement is utilized to adjust at least one of acoustic volume or acoustic focus.

18. The wearable optics device as in claim 10,
Wherein at least one of the sensors comprises a microphone is coupled using one or more of
By a wire, to a frame, or using a wireless connection.

19. The wearable optics device as in claim 18,
wherein the microphone is used in combination with one or more of a camera, an infrared camera, an imaging sensor.

20. The wearable optics device as in claim 10,
wherein at least one of the one or more sensors includes an earpiece containing a speaker with a microphone disposed to perform noise cancellation.

\* \* \* \* \*